US010939685B2

(12) United States Patent
Sinclair et al.

(10) Patent No.: US 10,939,685 B2
(45) Date of Patent: Mar. 9, 2021

(54) FUNGAL SPECIES, COMPOSITIONS DERIVED THEREFROM, AND USES THEREOF

(71) Applicant: President and Fellows of Harvard College, Cambridge, MA (US)

(72) Inventors: David A. Sinclair, Chestnut Hill, MA (US); Kyle S. Landry, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 159 days.

(21) Appl. No.: 16/091,279

(22) PCT Filed: Apr. 5, 2017

(86) PCT No.: PCT/US2017/026090
§ 371 (c)(1),
(2) Date: Oct. 4, 2018

(87) PCT Pub. No.: WO2107/176853
PCT Pub. Date: Oct. 12, 2017

(65) Prior Publication Data

US 2019/0110481 A1 Apr. 18, 2019

Related U.S. Application Data

(60) Provisional application No. 62/318,597, filed on Apr. 5, 2016.

(51) Int. Cl.

| | |
|---|---|
| ***A01N 63/30*** | (2020.01) |
| ***C09D 7/40*** | (2018.01) |
| ***C12Q 1/18*** | (2006.01) |
| ***A61K 38/43*** | (2006.01) |
| ***C12R 1/645*** | (2006.01) |
| *A61K 36/06* | (2006.01) |

(52) U.S. Cl.
CPC .............. *A01N 63/30* (2020.01); *A61K 38/43* (2013.01); *C09D 7/40* (2018.01); *C12Q 1/18* (2013.01); *C12R 1/645* (2013.01); *A61K 36/06* (2013.01)

(58) Field of Classification Search
CPC .............. C12Q 1/18; C12R 1/645; C09D 7/40
See application file for complete search history.

(56) References Cited

U.S. PATENT DOCUMENTS 4,426,396 A 1/1984 Young
6,448,062 B1 9/2002 Huth et al.
2013/0202581 A1* 8/2013 Fallon .................... A61P 17/02
424/94.21

FOREIGN PATENT DOCUMENTS

WO WO-2005/013898 A2 2/2005
WO WO-2009/155115 A2 12/2009
WO WO-2009155115 A2 * 12/2009 ............ A01N 63/10

OTHER PUBLICATIONS

International Search Report and Written Opinion for International Application No. PCT/US17/26090 dated Sep. 6, 2017.
Landry, "Purification and Characterization of Novel Nucleases from a Thermophilic Fungus," University of Massachusetts Amherst (2012).
Landry et al., "Characterization of a Recently Purified Thermophilic DNase from a Novel Thermophilic Fungus," Appl Biochem Biotechnol, 173:1587-1596 (2014).
Landry et al., "Development of a Novel Affinity Membrane Purification System for Deoxyribonuclease," Appl Biochem Biotechnol, 172:1964-1969 (2014).
"*Fungal* sp. TM417 18S ribosomal RNA gene, partial sequence; internal transcribed spacer 1 and 5.8S ribosomal RNA gene, complete sequence; and internal transcribed spacer 2, partial sequence," GenBank: KC462166.1.
Landry et al., "Purification and Characterization of Iso-Ribonucleases from a Novel Thermophilic Fungus," Int. J. Mol. Sci., 15:944-957 (2014).
Landry et al., "Purification of an Inducible DNase from a Thermophilic Fungus," Int. J. Mol. Sci., 15:1300-1314 (2014).

* cited by examiner

*Primary Examiner* — Heidi Reese
(74) *Attorney, Agent, or Firm* — Foley Hoag LLP

(57) ABSTRACT

Provided herein are secretory compositions/cocktails derived from a novel, extremophilic fungal species cultured, isolated, characterized and sequenced herein. Said novel, extremophilic fungal species may be exploited to produce a secretory compositions/cocktails which comprise a unique mixture of thermo-tolerant, stable enzymes capable of digesting cellular and genetic material in its surroundings under extreme temperatures. Such secretory compositions/cocktails may be useful as cleaning and sterilization solutions against biofilm, urine, yeast, bacterial, or viral contamination. Other uses include, but are not limited to, urea removal, fertilizer wastewaters, wastewater reclamation for life support systems in space, pH control, source of ammonia and carbon dioxide, starch digestion, biofuel production, as pharmaceuticals, and medical treatments such as wounds, skin disorders, or nail disorders.

16 Claims, 13 Drawing Sheets

FUNGAL SPECIES, COMPOSITIONS DERIVED THEREFROM, AND USES THEREOF

CROSS-REFERENCE

This application is a § 371 national-stage application based on PCT/US17/26090, filed Apr. 5, 2017, which claims the benefit of priority to U.S. Provisional Application Ser. No. 62/318,597, filed Apr. 5, 2016, each of which are hereby incorporated by reference in their entirety.

BACKGROUND

Thermophilic, psychrophilic, and mesophilic fungi may secrete a variety of enzymes useful for bioprocesses or other industrial applications. However, there has been very little effort to isolate, identify, and characterize new fungal species. Likewise, examination of extracellular production by thermophilic, psychrophilic, and mesophilic fungi has been sparse. While desirable characteristics of different fungal species could be exploited, the optimal conditions for culturing and enhancing potency of secretory enzymes vary greatly. Many variables influence the success of culturing, including but not limited to: temperature, pH, growth medium, lighting conditions, time periods, agitation, supplements and chemicals added. Identifying the small and unpredictable window of conditions suitable for isolating novel fungal species, while simultaneously generating compositions of enzymes having enhanced potency, high/low temperature optima, and stability, presents a significant challenge.

SUMMARY

Provided herein are secretory compositions derived from a novel, extremophilic fungal species cultured, isolated, characterized and sequenced herein. Said novel, extremophilic fungal species may be exploited to produce secretory compositions or "cocktail" of compositions (sometimes referred to herein as "compositions/cocktails") which comprise a unique mixture of thermo-tolerant, stable enzymes capable of digesting cellular and genetic material even under extreme temperatures. Such secretory compositions/cocktails may be useful as cleaning and sterilization solutions against biofilms, urine, yeast, metazoan, bacterial, or viral contamination. Other uses include, but are not limited to, urea removal, fertilizer wastewaters, wastewater reclamation for life support systems in space, pH control, source of ammonia and carbon dioxide, starch digestion, chitin digestion, cell digestion, biofuel production, as pharmaceuticals, and medical treatments such as wounds, skin disorders, or nail disorders. Additional properties may be provided by adding other proteins, peptides, chemicals or small molecules (e.g. lysozyme, ampD from *Bacillus* (a *Bacillus anthracis* killer) colloidal silver, other cell wall digestive enzymes, and proteases antimicrobial peptides) (See, for example, Bourguet et al. *Applied Environmental Microbiology.* 2012, and Vollmer et al. *FEMS Microbial Rev* 32 (2008) 259-286).

One aspect of the invention relates to a secretory composition derived from an extremophilic fungal species comprising one or more enzymes selected from the group consisting of urease, DNase, RNase, exonuclease, endonuclease, ribonuclease, amylase, acetoin reductase, an indole-3-acetamide hydrolase, a tryptophan monooxygenase, an acetolactate synthetase, an α-acetolactate decarboxylase, a pyruvate decarboxylase, a diacetyl reductase, a butanediol dehydrogenase, an aminotransferase, a tryptophan decarboxylase, an amine oxidase, an indole-3-pyruvate decarboxylase, an indole-3-acetaldehyde dehydrogenase, a tryptophan side chain oxidase, a nitrile hydrolase, a nitrilase, a peptidase, a protease, an adenosine phosphate isopentenyltransferase, a phosphatase, an adenosine kinase, an adenine phosphoribosyltransferase, CYP735A, a 5'ribonucleotide phosphohydrolase, an adenosine nucleosidase, a zeatin cis-trans isomerase, a zeatin 0-glucosyltransferase, a β-glucosidase, a cis-hydroxylase, a CK cis-hydroxylase, a CK N-glucosyltransferase, a 2,5-ribonucleotide phosphohydrolase, an adenosine nucleosidase, a purine nucleoside phosphorylase, a zeatin reductase, a hydroxylamine reductase, a 2-oxoglutarate dioxygenase, a gibberellic 2B/3B hydrolase, a gibberellin 3-oxidase, a gibberellin 20-oxidase, a chitosanase, a chitinase, a β-1,3-glucanase, a β-1,4-glucanase, a β-1,6-glucanase, an aminocyclopropane-1-carboxylic acid deaminase, chitosanase, a cellulase, a lipase, a lignin oxidase, a protease, a glycoside hydrolase, a phosphatase, a nitrogenase, a nuclease, an amidase, a nitrate reductase, a nitrite reductase, an amylase, an ammonia oxidase, a ligninase, a glucosidase, a phospholipase, a phytase, a pectinase, a glucanase, a sulfatase, a xylanase, an endocellulase, an exocellulase, a 3-glucosidase, phospholipase, acetate kinase, phosphotransacetylase, lactate dehydrogenase, pyruvate decarboxylase (PDC), alcohol dehydrogenase (ADH), xylose isomerase, xylulokinase, L-arabinose isomerase, L-ribulose-5-phosphate 4-epimerase, a glycan strand-cleaving enzyme/glycosidase, N-acetylglucosaminidase, acetylmuramyl-L-alanine amidase, lysozyme, lytic transglycosylase and peptidoglycan endopeptidase.

In some embodiments, the composition comprises ampD.

In some embodiments, the composition comprises lysozyme.

In some embodiments, the composition comprises phi29 lysozyme.

In some embodiments, the composition comprises two, three, four, five, six, seven, eight, nine, or ten enzymes.

In some embodiments, the one or more enzymes have a 25-, 30-, 35-, 40-, 45-, 50-, 55-, 60-, 65-, 70-, 75-, 80-, 85-, 90-, 95-, 100-, 105-, 110-, 115-, 120-, 125-, 130-, 135-, 140-, 145-, 150-, 155-, 160-, 165-, 170-, 175-, 180-, 185-, 190-, 195-, or 200-fold increase in specific activity when purified using size exclusion chromatography in combination with an affinity based membrane purification system.

In some embodiments, the one or more enzymes is 50%, 55%, 60%, 65%, 70%, 75%, 80%, 85%, 90%, 95%, 98%, or 99% pure.

In some embodiments, the extremophilic fungal species is 80%, 81%, 82%, 83%, 840%, 85%, 86%, 87%, 88%, 89%, 90%, 91%, 92%, 93%, 94%, 95%, 96%, 97%, 98%, 99.1%, 99.2%, 99.3%, 99.4%, 99.5%, 99.6%, 99.7%, 99.8% homologous to a known thermophilic, psychrophilic, ormesophilic fungal species.

In some embodiments, the thermophilic fungal species is selected from the group consisting of TM-417, *Zygomycetes, Absidia corymbifera, Mortierella turficola, M wolfi, Mucor miehei, M pusillus, Rhizomucor* sp., *Rhizopus arrhizus, Chaetomium* sp., *R. cohnii, R. microspores, Ascomycetes, Allescheria terrestris, Byssochlamys verrucosa, Chaetomium britannicum, C. thermophile, C. thermophile* var. *coprophile, C. thermophile* var. *dissitun, C. virginicum, Emericella nidulans, Hansenula polymorpha, Myriococcum albomyces, Sphaerospora saccata, Talaromyces byssochlamydoides, T emersonii, T leycettanus. T thermophiles, Thermoascus aurantiacus, T crustaceus, Thielavia australiensis,*

*T sepedonium, T thermophile, Basidiomyceles, Coprinus delicatulus, Mycelia Sterila, Burgoa-Papulaspora, Papulaspora thermophile, Deuteromycetes, Acremonium albamensis, Acrophialophora fusispora, Aspergillus candidus, A. fumigatus, Botrytis* sp., *Sphaerospora saccata, Calcarisporium thermophile, Cephalosporium* sp., *Allescheria terrestris, Cephalosponum* sp., *Thielavia australiensis, Geotrichum* sp. A, *Humicola grisea* var. *thermoidea, H. insolens, H. lanuginose, H. stellate, Malbranchea pulchella* var. *suljurea, Nodulisporium cylindroconium, Tritirachium* sp. *A. Paecilomyces crustaceus, Thermoascus, P. puntonii, P. variotii, Paecilomyces* sp., *Byssochlamys verrucosa, Paecilomyces* sp., *Talaromyces byssochlamydoides, Penicillium duponti Talaromyces thermophilus, P. emersonii Talaromyces, P. leycettanum Talaromyces, P. piceum, P. argillaceum, Ptychogaster* sp., *Sporotrichum pulverulentum, Scolecobasidium* sp. A, *Diplorhinotrichum galloparum, Sporotrichum thermophile, Thielavia, S. pulverulentum, Stilbella thermophile, Thermomyces ibadanesis, Torula thermophile, Torulopsis candida, Tritirachium* sp. A, and *Nodulisporium cylindroconium.*

In some embodiments, the thermophilic fungal species is TM-417.

In some embodiments, any of the compositions of the present invention as a clean solution. In some embodiments, any of the compositions of the present invention as a titratable self-destruct composition—slow release—slowdestruct.

In some embodiments, any of the compositions of the present invention as a slow release solution comprising any of the compositions of the present invention.

Another aspect of the invention relates to a recombinant extremophilic fungal species comprising at least one heterologous gene, said gene enhances or increases the potency of any of the compositions of the present invention. In some embodiments, the recombinant extremophilic fungal species comprises a mutation, substitution, deletion, addition, insertion, or replacement.

In some embodiments, the recombinant comprises at least two, three, four, or five, heterologous genes.

Another aspect of the invention relates to a method for treating a contaminated surface, comprising the step of contacting the contaminated surface with an effective amount of any of the compositions of the present invention.

In some embodiments, the contaminated surface comprises a biofilm, bacterial, fungal, viral, or yeast growth.

In some embodiments, the contaminated surface comprises *Bacillus anthracis.*

Another aspect of the invention relates to a method for decontaminating or sterilizing a product or system comprising the step of contacting the product or system with the composition of claim 1, wherein the product or system is selected from the group consisting of medical device, clinical product, agricultural specimen, environmental specimen, manufacturing sample, industrial system, transportation, marine system, and household system.

In some embodiments, the medical device is a catheter, stent, IV, or surgical tool. In some embodiments, the agricultural specimen is a food, farm product, water supply, waste water, fertilizer wastewater, or sludge.

In some embodiments, the environmental specimen is a lake, pond, fountain, or pool. In some embodiments, the clinical product is an artificial kidney dialysate.

In some embodiments, the manufacturing sample is a machine for processing samples.

In some embodiments, the industrial system is selected from the group consisting of a cooling water system, heat exchanger, pulp and paper manufacturing, food processing system, metalworking, photo processing, reverse osmosis membrane, water processing, flow channel, turbine, solar panel, pressurized water reactor, injection and spray nozzle, steam generator, process equipment, secondary oil recovery injection well, and piping.

In some embodiments, the marine system comprises offshore oil and gas pipeline, off-shore oil rig, environments within a cruise liner, boat or oil rig, or a boat hull.

In some embodiments, the household environment comprises cutting surface, sink, counter-top, shower, vase, pet food bowl, water bowl, decorative water landscaping, and bird baths.

Another aspect of the invention relates to a method for removing urea from a product or system comprising the step of contacting the product or system with the composition of claim 1, wherein the product or system is selected from the group consisting of medical device, clinical product, agricultural specimen, environmental specimen, manufacturing sample, industrial system, marine system, and household system.

Another aspect of the invention relates to a method for treating a wound comprising the step of contacting the surface of the injured area with a therapeutically effective amount of any of the compositions of the present invention.

In some embodiments, the wound is a cut, abrasion, open wound, sore, or abscess.

Another aspect of the invention relates to a method for treating a skin or nail disorder comprising the step of contacting the affected surface of the skin or nail with a therapeutically effective amount of any of the compositions of the present invention.

In some embodiments, the skin or nail disorder is selected from the group consisting of acne, actinic keratosis, alopecia areata, athlete's foot, onchomychosis, atopic dermatitis, osmidrosis, eczema, fungal infection of the nails, psoriasis, rosacea, slow wound healing, folliculitis, keratosis pilaris, perioral dermatitis, angiofibromas, cutaneous inflammation, aging damage, dyschromia, premature greying hair, and seborrhea.

Another aspect of the invention relates to a method of producing a biofuel comprising the step of contacting a biomass with an effective amount of the composition of any of the compositions of the present invention.

In some embodiments, the biofuel is selected from the group consisting of alcohol, ethanol, biodiesel, bioethanol, bioalcohol, green diesel, biofuel gasoline, vegetable oil, biogas, syngas, and solid biofuel.

In some embodiments, the biomass is selected from the group consisting of lignocellulosic material, woody biomass, recycled wood pulp fiber, sawdust, hardwood, softwood, algae, corn, sugarcane, sweet sorghum, trees, grass, switch grass, cord grass, rye grass, reed canary grass, miscanthus, sugar-processing residue, sugar cane bagasse; agricultural waste, rice straw, rice hulls, barley straw, corn cobs, cereal straw, wheat straw, canola straw, oat straw, oat hulls, corn fiber, stover, soybean stover, corn stover, forestry waste, recycled wood pulp fiber, sawdust, hardwood, poplar, oak, maple, birch, willow, softwood, manure, wastewater, cereal straws, wheat straw, barley straw, canola straw, oat straw, and corn fiber, or combinations thereof.

Another aspect of the invention relates to a method for reducing an amount or an activity of microorganisms, comprising: contacting a substrate comprising the microorganisms with a composition comprising one or more enzymes derived from an extremophilic fungal species, thereby reducing the amount or the activity of the microorganisms.

In some embodiments, the extremophilic fungal species is TM-417.

In some embodiments, the extremophilic fungal species is at least about 80% homologous to TM-417.

In some embodiments, the one or more enzymes comprise at least one enzyme selected from the group consisting of urease, DNase, RNase, exonuclease, endonuclease, ribonuclease, amylase, acetoin reductase, an indole-3-acetamide hydrolase, a tryptophan monooxygenase, an acetolactate synthetase, an α-acetolactate decarboxylase, a pyruvate decarboxylase, a diacetyl reductase, a butanediol dehydrogenase, an aminotransferase, a tryptophan decarboxylase, an amine oxidase, an indole-3-pyruvate decarboxylase, an indole-3-acetaldehyde dehydrogenase, a tryptophan side chain oxidase, a nitrile hydrolase, a nitrilase, a peptidase, a protease, an adenosine phosphate isopentenyltransferase, a phosphatase, an adenosine kinase, an adenine phosphoribosyltransferase, CYP735A, a 5'ribonucleotide phosphohydrolase, an adenosine nucleosidase, a zeatin cis-trans isomerase, a zeatin 0-glucosyltransferase, a β-glucosidase, a cis-hydroxylase, a CK cis-hydroxylase, a CK N-glucosyltransferase, a 2,5-ribonucleotide phosphohydrolase, an adenosine nucleosidase, a purine nucleoside phosphorylase, a zeatin reductase, a hydroxylamine reductase, a 2-oxoglutarate dioxygenase, a gibberellic 2B/3B hydrolase, a gibberellin 3-oxidase, a gibberellin 20-oxidase, a chitosanase, a chitinase, a β-1,3-glucanase, a β-1,4-glucanase, a β-1,6-glucanase, an aminocyclopropane-1-carboxylic acid deaminase, chitosanase, a cellulase, a lipase, a lignin oxidase, a protease, a glycoside hydrolase, a phosphatase, a nitrogenase, a nuclease, an amidase, a nitrate reductase, a nitrite reductase, an amylase, an ammonia oxidase, a ligninase, a glucosidase, a phospholipase, a phytase, a pectinase, a glucanase, a sulfatase, a xylanase, an endocellulase, an exocellulase, a β-glucosidase, phospholipase, acetate kinase, phosphotransacetylase, lactate dehydrogenase, pyruvate decarboxylase (PDC), alcohol dehydrogenase (ADH), xylose isomerase, xylulokinase. L-arabinose isomerase, L-ribulose-5-phosphate 4-epimerase, a glycan strand-cleaving enzyme/glycosidase, N-acetylglucosaminidase, acetylmuramyl-L-alanine amidase, lysozyme, lytic transglycosylase and peptidoglycan endopeptidase.

In some embodiments, the one or more enzymes comprise two or more enzymes.

In some embodiments, the one or more enzymes comprise three or more enzymes.

In some embodiments, the one or more enzymes comprise four or more enzymes.

In some embodiments, the one or more enzymes have at least about a 25-fold increase in specific activity when purified using size exclusion chromatography in combination with an affinity based membrane purification system.

In some embodiments, the one or more enzymes have at least about a 100-fold increase in specific activity when purified using size exclusion chromatography in combination with an affinity based membrane purification system.

In some embodiments, the one or more enzymes have at least about a 200-fold increase in specific activity when purified using size exclusion chromatography in combination with an affinity based membrane purification system.

In some embodiments, the one or more enzymes is at least about 50% pure.

In some embodiments, the one or more enzymes is at least about 75% pure.

In some embodiments, the one or more enzymes is at least about 95% pure.

In some embodiments, the composition comprises ampD.

In some embodiments, the composition comprises lysozyme.

In some embodiments, the composition comprises phi29 lysozyme.

In some embodiments, the microorganisms comprise bacteria, fungi, viruses, or yeast.

In some embodiments, the microorganisms comprise *Bacillus anthracis.*

In some embodiments, the activity of the microorganisms comprises pathogenicity.

In some embodiments, the activity of the microorganisms comprises viability.

In some embodiments, the activity of the microorganisms comprises reproduction.

In some embodiments, the activity of the microorganisms comprises metabolism.

In some embodiments, the activity of the microorganisms comprises toxin production.

In some embodiments, the amount or the activity of the microorganisms is reduced by at least about 10%.

In some embodiments, the amount or the activity of the microorganisms is reduced by at least about 50%.

In some embodiments, the amount or the activity of the microorganisms is reduced by at least about 700/%.

In some embodiments, the amount or the activity of the microorganisms is reduced by at least about 95%.

In some embodiments, the amount or the activity of the microorganisms is reduced by at least about 99%.

In some embodiments, the substrate comprises a liquid.

In some embodiments, the substrate comprises water.

In some embodiments, the substrate comprises a solid.

In some embodiments, the substrate comprises steel.

In some embodiments, the substrate comprises glass.

In some embodiments, the substrate is part of a product or system selected from the group consisting of medical device, clinical product, agricultural specimen, environmental specimen, manufacturing sample, industrial system, transportation, marine system, and household system.

In some embodiments, the medical device is a catheter, stent, IV, or surgical tool.

In some embodiments, the agricultural specimen is a food, farm product, water supply, waste water, fertilizer wastewater, or sludge.

In some embodiments, the environmental specimen is a lake, pond, fountain, or pool.

In some embodiments, the clinical product is an artificial kidney dialysate.

In some embodiments, the manufacturing sample is a machine for processing samples.

In some embodiments, the industrial system is a cooling water system, a heat exchanger, a pulp and paper manufacturing system, food processing system, a metalworking system, a photo processing system, a reverse osmosis membrane, a water processing system, a flow channel, a turbine, a solar panel, a pressurized water reactor, an injection and spray nozzle, a steam generator, process equipment, a secondary oil recovery injection well, or piping.

In some embodiments, the marine system comprises an offshore oil and gas pipeline, off-shore oil rig, environments within a boat or oil rig, or a boat hull.

In some embodiments, the household environment comprises a cutting surface, a sink, a counter-top, a shower, a vase, a pet food bowl, a water bowl, decorative water landscaping, or a bird bath.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 depicts the novel, extremophilic fungal cultures prior to extraction and stabilization of the enzyme cocktail.

FIG. 7 shows the antimicrobial activity of fungal extract with supplemental compounds.

DETAILED DESCRIPTION

I. Definitions

Figure 1A:
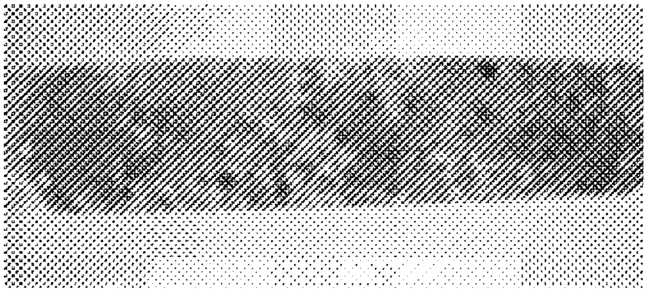
FIG. 1A shows balls of fungal hyphae produced in a rotating culture.

By "thermophilic" is meant an organism that is capable of growth and reproduction in higher temperatures, ranging from about 45° C. or higher.

By "mesophilic" is meant an organism that thrives and is capable of growth and reproduction in mild temperatures, ranging from about 20° C. to 45° C.

By "psychrophilic" or cryophiles are organisms that thrive and are capable of growth and reproduction in cold temperatures, ranging from about −20° C. to +20° C.

The term "homologous" refers to the "% homology" and is used interchangeably herein with the term "% identity" herein, and relates to the level of nucleic acid sequence identity between novel, extremophilic fungal species when compared to known thermophilic or mesophilic fungal species, when aligned using a sequence alignment program.

For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to about, 80%, 81%, 82%, 83%, 84%, 85%, 86%, 87%, 88%, 890%, 90%, 91%, 92%, 93%, 94%, 95%, 96%, 97%, 98%, 99.1%, 99.2%, 99.3%, 99.4%, 99.5%, 99.6%, 99.7%, 99.8% or more sequence identity of a novel, extremophilic fungal species when compared to known thermophilic or mesophilic fungal species.

Exemplary computer programs which can be used to determine identity between two sequences include, but are not limited to, the suite of BLAST programs, e.g., BLASTN, BLASTX, and TBLASTX, BLASTP and TBLASTN, publicly accessible at www.ncbi.nlm.nih.gov/BLAST.

Sequence searches are typically carried out using the BLASTN program when evaluating a given nucleic acid sequence relative to nucleic acid sequences in the GenBank DNA Sequences and other public databases. The BLASTX program can be used for searching nucleic acid sequences that have been translated in all reading frames against amino acid sequences in the GenBank Protein Sequences and other public databases.

The term "therapeutic effect" refers to a local or systemic effect in animals, particularly mammals, and more particularly humans, caused by a pharmacologically active substance.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The term "treating" a disease in a subject or "treating" a subject having a disease refers to subjecting the subject to a pharmaceutical treatment, e.g., the administration of a secretory compositions/cocktails of the present invention, such that at least one symptom of the disease is decreased, prevented from worsening, or delayed from worsening. An "effective amount" or "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

II. Methods for Identifying Novel Fungal Species

Aspects of the present invention relate to methods for isolating and identifying novel, extremophilic fungal species. Such methods may comprise the placement of natural or unnatural nutrient sources within the environment to allow for concentration of the species at a site for collection, then within laboratory conditions, varying culture, plate, media, temperature, time periods, pH, or lighting conditions, or combinations thereof. Such methods may also comprise varying oxygen, carbon dioxide, carbon source, nitrogen source, fatty acid, nucleic acid, nutrient, vitamin, trace mineral, salt, ion, or amino acid levels, or combinations thereof.

In some embodiments, the temperature for incubating, culturing, or assaying components of the secretory compositions/cocktails may be −45° C., −40° C., −35° C., −30° C., −25° C., −20° C., −15° C., −10° C., −5° C., 0° C., 5° C., 10° C., 15° C., 20° C., 25° C., 30° C., 35° C., 40° C., 45° C., 50° C., 55° C., 60° C., 65° C., 70° C., 75° C., 80° C., 85° C., 90° C., 95° C., or 100° C. In certain embodiments, the invention relates to any one of the above-mentioned methods, wherein the temperature is from about 30° C. to about 75° C. In certain embodiments, the invention relates to any one of the above-mentioned methods, wherein the temperature is from about 45° C. to about 75° C. In certain embodiments, the invention relates to any one of the above-mentioned methods, wherein the temperature is from about 55° C. to about 65° C. In certain embodiments, the invention relates to any one of the above-mentioned methods, wherein the temperature is about 45° C. In certain embodiments, the invention relates to any one of the above-mentioned methods, wherein the temperature is about 55° C. In certain embodiments, the invention relates to any one of the above-mentioned methods, wherein the temperature is about 65° C.

In some embodiments, the temperature for incubating, culturing, or assaying components of the secretory compositions/cocktails may be performed for 1 day, 2 days, 3 days, 4 days, 5 days, 6 days, 7 days, 8 days, 9 days, 10 days, 11 days, 12 days, 13 days, or 14 days.

In some embodiments, the media may comprise oatmeal, water, yeast, glucose, cellulose, and Czapek's agar. In some embodiments, the media may be supplemented with an antibiotic selected from the group consisting of penicillin-G, ampicillin, streptomycin. In some embodiments, the media may be supplemented with reagent to allow for color detection, such as methyl green. In some embodiments, the media may be supplemented to enhance the production of specific enzymes, such as DNA to encourage the production on DNAses, or whole cells or components of bacterial or viral species to encourage enzymes that inhibit or kill pathogens.

In some embodiments, the pH may be about 2.0, 3.0, 4.0, 5.0, 6.0, 7.0, 8.0, 9.0, or 10.0 and ±0.01, ±0.02, ±0.03, ±0.04, ±0.05, ±0.06, ±0.07, ±0.08, ±0.09, ±0.1, ±0.2, ±0.3, ±0.4, ±0.5, ±0.6, ±0.7, ±0.8, or ±0.9. In certain embodiments, the invention relates to any one of the above-mentioned methods, wherein the pH is between about 5 and about 9. In certain embodiments, the invention relates to any one of the above-mentioned methods, wherein the pH is between about 6 and about 8. In certain embodiments, the invention relates to any one of the above-mentioned methods, wherein the pH is about 5, about 6, about 7, about 8, or about 9. In certain embodiments, the invention relates to any one of the above-mentioned methods, wherein the pH is about 6, about 7, or about 8. In certain embodiments, the invention relates to any one of the above-mentioned methods, wherein the pH is about 7.

In some embodiments, the media may be enriched with nucleic acids, sugars, carbohydrates, fatty acids and lipids, DNA, deoxyribose, proteinase K, lysozyme (e.g., phi29 lysozyme) or antimicrobial chemicals or peptides (e.g. microsilver, antibiotics, or ampD from *Bacillus* species such as *Bacillus cereus* E33L) during the incubating, culturing, purification, assaying, or other production steps. In some embodiments, enzymes that digest bacterial cell walls including glycan strand-cleaving enzymes (glycosidases) including N-acetylglucosaminidases, lysozymes and lytic transglycosylases. These include the N-acetylmuramyl-L-alanine amidases and peptidoglycan endopeptidases (Vollmer et al, 2008).

In some embodiments, the amount of DNA, RNA, deoxyribose or other nucleic acids, added may be 0.1, 0.2, 0.3, 0.4, 0.5, 0.6, 0.7, 0.8, 0.9, or 1.0 g. Such enrichment may increase potency of the isolated fungal species and/or any of the components of the secretory compositions/cocktails. In some embodiments, the culture may be supplemented with $Na^+$, $K^+$, $Mg^{++}$, or $Ca^{++}$. In some embodiments, the ratio of the $Mg^{++}$ to $Ca^{++}$ or $Na^+$ to $K^+$ may be 1:1, 1:2, 2:1, 1:3, 3:1, 1:4, 4:1, 1:5, 5:1, 1:6, 6:1, 1:7, 7:1, 1:8, 8:1, 1:9, 9:1, 1:10, or 10:1. For example, addition of $Ca^{++}$ may prolong the survival and activity of certain enzymes (i.e., $Ca^{2+}$ protects DNAses against digestion by proteases), whereas no $Ca^{++}$ leads to a shortened lifespan of certain enzymes (due to diminished protection against digestion byproteases). Modifications of the $Ca^{++}$ concentrations and/or ratios of the [$Ca^{++}$] to [$Mg^{++}$] can prolong or shorten the life of enzymes within the extract.

In some embodiments, the fungal culture is subject to agitated growth, static growth, or altering static and agitated growth. In some embodiments, the agitation is at 50 rpm, 75 rpm, 100 rpm, 125 rpm, 150 rpm, 175 rpm, or 200 rpm. In some embodiments, the fungal culture is subject to continuous culture or non-continuous culture.

In some embodiments, the lighting conditions are varied to encourage spore formation, including prolonging or shortening duration of exposure to light for 1 hour, 2 hours, 3 hours, 4 hours, 5 hours, 6 hours, 7 hours, 8 hours, 9 hours, 10 hours.

In some embodiments, the sample used as source for fungal species may comprise compost. In some embodiments, the sample may be incubated on yeast protein soluble starch agar plates comprising yeast extract, $K_2HPO_4$, $MgSO_4$, soluble starch, and a pH about 7, among others. In some embodiments, antibiotics selected from the group consisting of polymyxin B, penicillin G, ampicillin, and streptomycin may be added at 5 ppm, 10 ppm, 15 ppm, 20 ppm, 25 ppm, 30 ppm, 35 ppm, 40 ppm, 45 ppm, or 50 ppm.

III. Extremophilic Fungal Species

Extremophilic fungal species identified, isolated, and characterized by the methods set forth herein may encompass fungal species homologous to known thermophilic, psychrophilic, and mesophilic fungi. In one embodiment, the novel, extremophilic fungal species is described in Example 1, and characterized by the bacterial properties set forth in Example 2.

Extremophilic fungi and other extremophilic organisms such as extremophilic bacteria may be useful in process applications in biotechnology, such as the methods of the present invention, stemming from their ability to grow at relatively high temperatures with attendant high metabolic rates, production of physically and chemically stable enzymes, and elevated yields of end products. In some cases, the extremophilic fungus is TM-417. Other thermophilic fungal species may include, but not limited to, *Zygomycetes, Absidia corymbifera, Mortierella turficola, M wolfi, Mucor miehei, M pusillus, Rhizomucor* sp., *Rhizopus arrhizus, Chaetomium* sp., *R. cohnii, R. microspores, Ascomycetes, Allescheria terrestris, Byssochlamys verrucosa, Chaetomium britannicum, C. thermophile, C. thermophile* var. *coprophile, C. thermophile* var. *dissitum, C. virginicum,*

*Emericella nidulans, Hansenula polymorpha, Myriococcum albomyces, Sphaerospora saccata, Talaromyces byssochlamydoides, T emersonii, T leycettanus, T thermophiles, Thermoascus aurantiacus, T crustaceus, Thielavia australiensis, T sepedonium, T thermophile, Basidiomycetes, Coprinus delicatulus, Mycelia Sterila, Burgoa-Papulaspora, Papulaspora thermophile, Deuteromycetes, Acremonium albamensis, Acrophialophora fusispora, Aspergillus candidus, A. fumigatus, Botrytis* sp., *Sphaerospora saccata, Calcarisporium thermophile, Cephalosporium* sp., *Allescheria terrestris, Cephalosporium* sp., *Thielavia australiensis, Geotrichum* sp. *A. Humicola grisea* var. *thermoidea, H. insolens, H. lanuginose, H. stellate, Malbranchea pulchella* var. *suljurea, Nodulisporium cylindroconium, Tritirachium* sp. *A. Paecilomyces crustaceus, Thermoascus, P. puntonii, P. variotii, Paecilomyces* sp., *Byssochlamys verrucosa, Paecilomyces* sp., *Talaromyces byssochlamydoides, Penicillium duponti Talaromyces thermophilus, P. emersonii Talaromyces, P. leycettanum Talaromyces, P. piceum, P. argillaceum, Ptychogaster* sp., *Sporotrichum pulverulentum, Scolecobasidium* sp. *A, Diplorhinotrichum galloparum, Sporotrichum thermophile, Thielavia, S. pulverulentum, Stilbella thermophile, Thermomyces ibadanesis, Torula thermophile, Torulopsis candida, Tritirachium* sp. *A, and Nodulisporium cylindroconium.*

In certain embodiments, the fungal species may be 60%, 65%, 70%, 75%, 80%, 81%, 82%, 83%, 84%, 85%, 86%, 87%, 88%, 89%, 90, 91%, 92%, 93%, 94%, 95%, 96%, 97%, 98%, 99% homologous to any of the aforementioned mentioned thermophilic and mesophilic fungi. In some embodiment, the fungal species may be 60%, 65%, 70%, 75%, 80%, 81%, 82%, 83%, 84%, 85%, 86%, 87%, 88%, 89%, 90, 91%, 92%, 93%, 94%, 95%, 96° %, 97%, 98%, 99% homologous to any of the following *Clostridium thermocellum, Clostridium cellolyticum, Thermoanaerobacterium saccharolyticum, Clostridium stercorarium, Clostridium stercorarium* 11, *Caldiscellulosiruptor krisjanssonii*, and *Clostridium phytofermentans; Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brockii, Thermoanaerobacterium thermosaccharolyticum, Thermoanaerobacter thermohydrosulfuricus, Thermoanaerobacter ethanolicus, Thermoanaerobacter brocki, Clostridium thermocellum, Clostridium cellulolyticum, Clostridium phytofermentans, Clostridium straminosolvens, Geobacillus thermoglucosidasius, Geobacillus stearothermophilus, Saccharococcus caldoxylosilyticus, Saccharoccus thermophilus, Paenibachllus campinasensis, Bacillus flavothermus, Anoxybacillus kamchatkensis, Anoxybacillus gonensis, Caldicellulosiruptor acetigenus, Caldicellulosiruptor saccharolyticus, Caldicellulosinruptor krisjanssonii, Caldicellulosiruptor owensensis, Caldicellulosiruptor lactoaceticus, Anaerocellum thermophilum*, or *Chaetomium cellulolyticum.*

Major groups of thermophilic bacteria include eubacteria and archaebacteria. Thermophilic eubacteria include: phototropic bacteria, such as cyanobacteria, purple bacteria, and green bacteria; Gram-positive bacteria, such as *Bacillus, Clostridium*, Lactic acid bacteria, and *Actinomyces*; and other eubacteria, such as *Thiobacillus*, Spirochete, *Desulfotomaculum*, Gram-negative aerobes, Gram-negative anaerobes, and *Thermotoga*. Within archaebacteria are considered Methanogens, extreme thermophiles (an art-recognized term), and *Thermoplasma*. In some embodiments, the invention relates to identifying, characterizing, and isolating extremophilic bacteria related to or homologous to Gram-negative organotrophic thermophiles of the genera *Thermus*, Gram-positive eubacteria, such as genera *Clostridium*, and also which comprise both rods and cocci, genera in group of eubacteria, such as *Thermosipho* and *Thermotoga*, genera of Archaebacteria, such as *Thermococcus, Thermoproteus* (rod-shaped), *Thermofilum* (rod-shaped), *Pyrodictium, Acidianus, Sulfolobus, Pyrobaculum, Pyrococcus, Thermodiscus, Staphylothermus, Desulfurococcus, Archaeoglobus*, and *Methanopyrus*. In some embodiments, the invention relates to identifying, characterizing, and isolating extremophilic bacteria related to or homologous to thermophilic fungus including, but are not limited to: *Clostridium thermosulfurogenes, Clostridium cellulolyticum, Clostridium thermocellum, Clostridium thermohydrosulfuricum, Clostridium thermoaceticum, Clostridium thermosaccharolyticum, Clostridium tartarivorum, Clostridium thermocellulaseum, Clostridium phytofermentans, Clostridium straminosolvens, Thermoanaerobacterium thermosaccarolyticum, Thermoanaerobacterium saccharolyticum, Thermobacteroides acetoethylicus, Thermoanaerobium brockii, Methanobacterium thermoautotrophicum, Anaerocellum thermophilium, Pyrodictium occultum, Thermoproteus neutrophiuls, Thermofilum librum, Thermothrix thioparus, Desulfovibrio thermophilus, Thermoplasma acidophilum, Hydrogenomonas thermophilus, Thermomicrobium roseum, Thermus flavas, Thermus ruber, Pyrococcus furiosus, Thermus aquaticus, Thermus thermophilus, Chloroflexus aurantiacus, Thermococcus litoralis, Pyrodictium abyssi, Bacillus stearothermophilus, Cyanidium caldarium, Mastigocladus laminosus, Chlamydothrix calidissima, Chlamydothrix penicillata, Thiothrix carnea, Phormidium tenuissimum, Phormidium geysericola, Phormidium subterraneum, Phormidium bijahensi, Oscillatoria filiformis, Synechococcus lividus, Chloroflexus aurantiacus, Pyrodictium brocki, Thiobacillus thiooxidans, Sulfolobus acidocaldarius, Thiobacillus thermophilica, Bacillus stearothermophilus, Cerrosulcifer hamathensis, Vahlkampfia reichi, Cyclidium citrullus, Dactylaria gallopava, Synechococcus lividus, Synechococcus elongatus, Synechococcus minervae, Synechocystis aquatilus, Aphanocapsa thermalis, Oscillatoria terebriformis, Oscillatoria amphibia, Oscillatoria germinata, Oscillatoria okenii, Phormidium laminosum, Phormidium parparasiens, Symploca thermalis, Bacillus acidocaldarias, Bacillus coagulans, Bacillus thermocatenalatus, Bacillus licheniformis, Bacillus pamilas, Bacillus macerans, Bacillus circulans, Bacillus laterosporus, Bacillus brevis, Bacillus subtilis, Bacillus sphaericus, Desulfotomaculum nigrificans, Streptococcus thermophilus, Lactobacillus thermophilus, Lactobacillus bulgaricus, Bifidobacterium thermophilum, Streptomyces fragmentosporus, Streptomyces thermonitrificans, Streptomyces thermovulgaris, Pseudonocardia thermophila, Thermoactinomyces vulgaris, Thermoactinomyces sacchari, Thermoactinomyces candidas, Thermomonospora curvata, Thermomonospora viridis, Thermomonospora citrina, Microbispora thermodiastatica, Microbispora aerata, Microbispora bispora, Actinobifida dichotomica, Actinobifida chromogena, Micropolyspora caesia, Micropolyspora faeni, Micropolyspora cectivugida, Micropolyspora cabrobrunea, Macropolyspora thermovirida, Micropolyspora viridinigra, Methanobacterium thermoautothropicum, Caldicellulosiruptor acetigenus, Caldicellulosiruptor saccharolyticus, Caldicellulosiruptor kristjanssonii, Caldicellulosiruptor owensensis, Caldicellulosiruptor lactoaceticus*, variants thereof, or progeny thereof.

In certain embodiments, the invention relates to a method of identifying, characterizing, and isolating extremophilic bacteria related or homologous to the genera *Thermoanaerobacterium* or *Thermoanaerobacter*, including, but not limited to, species selected from the group consisting of: *Thermoanaerobacterium thermosulfurigenes, Thermoanaerobacterium aotearoense, Thermoanaerobacterium polysaccharolyticum, Thermoanaerobacterium zeae, Thermoanaerobacterium xylanolyticum, Thermoanaerobacterium saccharolyticum, Thermoanaerobium brocki, Thermoanaerobacterium thermosaccharolyticum, Thermoanaerobacter thermohydrosulfuricus, Thermoanaerobacter ethanolicus, Thermoanaerobacter brockii*, variants thereof, and progeny thereof.

In certain embodiments, the invention relates to a method of identifying, characterizing, and isolating extremophilic bacteria related to or homologous to the genera *Geobacillus, Saccharococcus, Paenibacillus, Bacillus*, and *Anoxybacillus*, including, but not limited to, species selected from the group consisting of: *Geobacillus thermoglucosidasius, Geobacillus stearothermophilus, Saccharococcus caldoxylosilyticus, Saccharoccus thermophilus, Paenibacillus campinasensis, Bacillus flavothermus, Anoxybacillus kamchatkensis, Anoxybacillus gonensis*, variants thereof, and progeny thereof.

In certain embodiments, the invention relates to a method of identifying, characterizing, and isolating extremophilic bacteria related to or homologous to the genera selected from the group consisting of *Saccharophagus degradans; Flavobacterium johnsoniae; Fibrobacter succinogenes; Clostridium hungatei; Clostridium phytofermentans; Clostridium cellulolyticum; Clostridium aldrichii; Clostridium termitididis; Acetivibrio cellulolyticus; Acetivibrio ethanolgignens; Acetivibrio multivorans; Bacteroides cellulosolvens*; and *Alkalibacter saccharofomentans*, variants thereof and progeny thereof.

IV. Recombinant Extremophilic Fungal Species or Recombinant Expression of Fungal Genes In one embodiment, the invention relates to recombinant, extremophilic fungal species, wherein the isolated novel extremophilic fungus is genetically-modified. These can be prepared by deleting or inactivating one or more genes, or adding novel genes from other species, optionally followed by a growth-based selection for mutants with improved performance or potency for producing enzymes and other antimicrobial molecules, such as proteases, lipases, glycan strand-cleaving enzymes (glycosidases), antimicrobial peptides, and cellulases. In certain embodiments, the genetically-modified extremophilic fungal species is modified to produce enzymes known to inhibit the growth or kill microbial species (e.g. ampD, lysozymes such as phi29 lysozyme). These proteins may be enhanced by adding bacterial targeting peptides that bind the enzymes to the cell surface of targeted organisms. In other embodiments, the genetically-modified extremophilic fungal species used in the methods of the invention can be cultured using any of the aforementioned conditions set forth in herein. In some embodiments, the genetically modified/recombinant extremophilic fungal species can be selected by a growth-based procedure to produce enzymes most efficiently at certain conditions (variations, in pH, temperature, light, $CO_2$, $O_2$, salt, nutrient, $Ca^{++}$ levels, nutrient, growth factors, proteinase K, lysozyme such as phi29 lysozyme). In certain embodiments, the genetically-modified extremophilic fungal species used in the methods of the invention can be selected by a growth-based procedure to produce enzymes most efficiently at about 45° C., 50° C., 55° C., 60° C., or 65° C. In certain embodiments, the genetically-modified extremophilic fungal species used in the methods of the invention can be selected by a growth-based procedure to produce enzyme most efficiently at a certain pH. In certain embodiments, the genetically-modified microorganisms used in the methods of the invention can be selected by a growth-based procedure to produce enzyme most efficiently at about pH 7.

In certain embodiments, the recombinant extremophilic fungal species may comprise at least one heterologous gene, wherein said heterologous gene is expressed at sufficient levels to increase the ability of said recombinant extremophilic fungal species to enhance production or potency of secreting enzymes or to confer upon said recombinant microorganism (which may be thermophilic) the ability to enhance production or potency of secreting enzymes. In some embodiments, the recombinant extremophilic fungal species may comprise at least two, three, four or five heterologous genes.

In another embodiment, genes from the extremophilic fungal species may be isolated and introduced into other species for protein production using the native sequence, or with improved properties though genetic modification. These improvements may include improved codon usage and expression levels, improved secretion, targeting peptides, increased activity, increased stability. Organisms that may be used for expression include yeasts (e.g. *Saccharomyces cerevisiae* and *Pichia pastoris*), bacteria (e.g. *E. coli*) and insect cells (e.g. baculovirus protein expression systems).

V. Secretory Compositions Cocktails Derived from Fungal Species

Novel, extremophilic fungal species identified, characterized, and isolated according the methods of the present invention have a variety of growth characteristics that can be exploited to provide a unique combination of enzymes, heat-resistant lipases, proteases, RNases and DNases that destroy biological material within minutes upon contact. Secretory compositions/cocktails derived from fungal species may be purified from cultures which can be grown in broth comprising yeast extract, $K_2HPO_4$, $MgSO_4$, soluble starch, methyl green, DNA salmon sperm; agar, and adjusted to pH 7.3. Cell mass may be removed from the sample comprising secretory compositions/cocktails by vacuum filtration through coarse filter paper (such as Fisherbrand Filter Paper P8). The cell mass may also be lysed and used for the production of enzymes that are not secreted. The filtrate may be filtered under vacuum through medium (Fisherbrand Filter Paper PS), and then through fine filter paper (Fisherbrand Filter Paper P2). The filtered sample may comprise a mixture of crude enzymes. To inhibit any bacterial and/or fungal growth, 0.02% sodium azide may be added to the crude enzyme sample. All crude enzyme samples may be stored at ambient temperature. In some embodiments, the crude enzyme samples comprising secretory compositions/cocktails may be dried or freeze-dried. In some embodiments, the dried secretory compositions/cocktails may be reconstituted prior to use.

In some embodiments, the secretory compositions/cocktails may be protected in microspheres. Such embodiments, may comprise balls of chitin, which are digested slowly by lysozyme.

In some embodiments, additional purification and/or concentration steps may be performed on the secretory compositions/cocktails. For example, such steps may comprise membrane preparation (e.g., using 47 mm, 0.2 μm FP-Vericel membrane, membrane filtration unit under vacuum, ultrafiltration membrane concentration, dialysis, pressure cell (e.g., via Amicon pressure cell), cellulose membrane (e.g., having a 1 kDa, 2 kDa, 3 kDa, 4 kDa, 5 kDa, 10 kDa, 15 kDa, 20 kDa cutoff), sephadex column chromatography, and affinity membrane purification (e.g. DNA coated membrane), or combinations thereof. Such steps may also include the use of tangential flow systems with polyethersulfone and/or Composite Regenerated Cellulose membranes/filters (e.g. the Pellicon system, Millipore). Such combinations of purification, filtration, concentration, dialysis steps may lead to a 25-, 30-, 35-, 40-, 45-, 50-, 55-, 60-, 65-, 70-, 75-, 80-, 85-, 90-, 95-, 100-, 105-, 110-, 115-, 120-, 125-, 130-, 135-, 140-, 145-, 150-, 155-, 160-, 165-, 170-, 175-, 180-, 185-, 190-, 195-, or 200-fold increase in specific activity, with 25%±5, ±10, or ±15 of the initial enzyme activity. In some embodiments, the secretory compositions/cocktails may be concentrated directed from the media, i.e., crude sample. In some embodiments, the secretory compositions/cocktails may be 50%, 55%, 60%, 65%, 70%, 75%, 80%, 85%, 90%, 95%, 98%, or 99% pure of the desired enzyme.

Secretory compositions/cocktails derived from fungal species as provided herein may comprising any of the following enzymes, proteases, and the like, alone or in any combination, including, but not limited to, urease, DNase, RNase, exonuclease, endonuclease, ribonuclease, chitinase, amylase, acetoin reductase, an indole-3-acetamide hydrolase, a tryptophan monooxygenase, an acetolactate synthetase, an α-acetolactate decarboxylase, a pyruvate decarboxylase, a diacetyl reductase, a butanediol dehydrogenase, an aminotransferase, a tryptophan decarboxylase, an amine oxidase, an indole-3-pyruvate decarboxylase, an indole-3-acetaldehyde dehydrogenase, a tryptophan side chain oxidase, a nitrile hydrolase, a nitrilase, a peptidase, a protease, an adenosine phosphate isopentenyltransferase, a phosphatase, an adenosine kinase, an adenine phosphoribosyltransferase, CYP735A, a 5'ribonucleotide phosphohydrolase, an adenosine nucleosidase, a zeatin cis-trans isomerase, a zeatin 0-glucosyltransferase, a β-glucosidase, a cis-hydroxylase, a CK cis-hydroxylase, a CK N-glucosyltransferase, a 2,5-ribonucleotide phosphohydrolase, an adenosine nucleosidase, a purine nucleoside phosphorylase, a zeatin reductase, a hydroxylamine reductase, a 2-oxoglutarate dioxygenase, a gibberellic 2B/3B hydrolase, a gibberellin 3-oxidase, a gibberellin 20-oxidase, a chitosanase, a chitinase, a β-1,3-glucanase, a β-1,4-glucanase, a β-1,6-glucanase, an aminocyclopropane-1-carboxylic acid deaminase, chitosanase, a cellulase, a lipase, a lignin oxidase, a protease, a glycoside hydrolase, a phosphatase, a nitrogenase, a nuclease, an amidase, a nitrate reductase, a nitrite reductase, an amylase, an ammonia oxidase, a ligninase, a glucosidase, a phospholipase, a phytase, a pectinase, a glucanase, a sulfatase, a urease, a xylanase, an endocellulase, an exocellulase, a β-glucosidase, phospholipase, acetate kinase, phosphotransacetylase, lactate dehydrogenase, pyruvate decarboxylase (PDC), alcohol dehydrogenase (ADH), xylose isomerase, xylulokinase, L-arabinose isomerase, or L-ribulose-5-phosphate 4-epimerase, glycan strand-cleaving enzymes (glycosidases) including N-acetylglucosaminidases, acetylmuramyl-L-alanine amidases, lysozymes, lytic transglycosylases, and peptidoglycan endopeptidases. The specific activity of any of the aforementioned enzymes, proteases, and the like, may be assayed using methods known in the art.

VI. Applications/Uses

One aspect of the invention relates to a method utilizing any one of the above-mentioned extremophilic fungal species or genetically-modified/recombinant extremophilic fungal species to produce certain secretory compositions/cocktails most efficiently under appropriate culture, incubation, or assay conditions. Such secretory compositions/cocktails may be useful in a variety of bioprocess, cleaning/sterilization, industrial, agricultural, and pharmaceutical/medical and commercial application, household applications set forth herein. Exemplary applications/uses of the secretory compositions/cocktails are provided below.

A. Cleaning/Sterilization Compositions

One aspect of the invention relates to use of the secretory compositions/cocktails described herein as cleaning/sterilization compositions.

As used herein, "affected surface" means that the surface is at least partially covered by contamination, including microorganism contamination, e.g., biofilm, yeast, viral, fungal, bacterial, protein, extracellular matrices, and the like, or is a surface prone to developing a biofilm, bacteria, and the like, thereon (e.g., is present in an aqueous or moist environment where contamination has formed in the past) or is a surface where prevention of contamination is desired (e.g., is present in an aqueous or moist environment). "Removing" can include removing all or a portion of the contamination as well as reducing the thickness of contamination by successively removing layers of organisms, thereby exposing additional contamination layer(s) below. Once removed from the affected surface, the detached contamination can be rinsed away, flushed, or otherwise transported from the affected environment (e.g., water system).

Treatment of a surface or other substrate can reduce the amount of contaminating microorganisms on the substrate. Such treatment can reduce the amount of microorganisms on the substrate by at least about 10%, 20%, 30%, 40%, 50%, 60%, 70%, 80%, 90%, 95%, 96%, 97%, 98%, 99%, 99.9%, 99.99%, 99.999%, or 100%. Treatment of a surface or other substrate can reduce the activity of contaminating microorganisms on the substrate. Such treatment can reduce the activity of microorganisms on the substrate by at least about 10%, 20%, 30%, 40%, 50%, 60%, 70%, 80%, 90%, 95%, 96%, 97%, 98%, 99%, 99.9%, 99.99%, 99.999%, or 100%. Activity can include but is not limited to pathogenicity, viability, reproduction, metabolism, toxin production, or other activity.

The compositions can be used to prevent the buildup of contamination on a surface, especially a surface prone to contamination formation. As used herein, "preventing" means prophylactically inhibiting the formation or re-formation of contamination on a surface. Preventing can include permanent or temporary cessation of contamination formation, as well as retardation or slowing of growth of biofilm, bacteria, or the like.

Thus, one aspect of the invention relates to method for treating a biofilm-affected surface, comprising the step of contacting the affected surface with an effective amount of any of the aforementioned secretory compositions/cocktails. The secretory compositions/cocktails can effectively penetrate through the biofilm layers, including the matrix, to successfully reach the surface underneath to disrupt the biofilm's attachment sites.

In some embodiments, an affected surface may be part of an industrial, marine, or household environment. In some embodiment, an affected surface may be selected from the group consisting of cooling water systems, heat exchangers, pulp and paper manufacturing, food processing systems, metalworking, photo processing, reverse osmosis membranes, water processing, flow channels, turbines, solar panels, pressurized water reactors, injection and spray nozzles, steam generators, process equipment, secondary oil recovery injection wells, and piping. In some embodiment, an affected surface may be a marine system selected from the group consisting of pipelines, oil-rigs, and boat hulls. In some embodiment, an affected surface is a household system selected from the group consisting of swimming pools, toilets, household drains, cutting surfaces, sinks, urinals, counter-tops, shower and bath surfaces, vases, pet food or water bowls, decorative water landscaping, and bird baths. In some embodiments, an affected surface comprises a material selected from the group consisting of metal, stainless steel, plastic, ceramic, porcelain, rubber, wood, concrete, cement, rock, marble, gypsum, and glass. In some embodiment, the step of contacting includes pouring, spraying, applying, squirting, dosing, dipping, cleaning, soaking, dousing, washing, covering, misting, scattering, spreading, flushing, injecting, incorporating, or spraying.

For example, planktonic microbes (e.g., bacteria, fungi) can adhere to virtually all natural and synthetic surfaces, with many of such microbes forming permanent attachments. It is commonly believed that microbes prefer to live as sessile organisms rather than in planktonic form because life in a sessile state facilitates development of unique survival mechanisms not found in their planktonic counterparts. Generally recognized as the first step in biofilm formation, microbial adhesion stimulates the production of extracellular matrix polymers, colloquially referred to as "slime" due to their slimy feel and appearance. This matrix further strengthens adhesion, provides protection to the sessile microbial population, and facilitates recruitment and growth of additional microbes to the biofilm community.

As the biofilm matures, successive microbe layers are added on top of one another, forming a multi-layered microbial system. A biofilm may comprise a vast number of different microorganism types or may include a specific microorganism as the predominant microbe. Biofilms also commonly include various abiotic materials (e.g., rust, dirt) that have become embedded in the biofilm matrix. Common biofilms found in industrial and household settings include those colonized by organisms selected from the bacterial genera *Pseudomonas, Staphylococcus, Aeromonas*, and *Klebsiella*, the family Enterobacteriaceae (including, e.g., *Escherichia coli*), and the fungi genera *Aspergillus, Penicillium, Myceliophthora, Humicola, Irpex, Fusarium, Stachybotrys, Scopiulariopsis, Chaetomium, Mycogone, Verticillium, Myrothecium, Papulospora, Gliocladium, Cephalosporium, Acremonum*, and combinations thereof.

Biofilms are extremely complex microbial ecosystems. When colonized into a biofilm, the behavior, structure, and physiology of microbes change dramatically, resulting in a number of potential advantages not possessed by the free-floating, planktonic form. Because of their enhanced survival mechanisms, biofilms can quickly respond and adapt to changing internal and external conditions, making their removal and prevention especially difficult. Biofilm structure and the physiological attributes of microorganisms within the biofilm also provide an intrinsic tolerance to antimicrobial agents (e.g., antibiotics, disinfectants, germicides, antifungals). When biofilm is removed from a surface via traditional means, such as by vigorous mechanical scrubbing with an industrial cleaner and/or disinfectants, a few "persister" cells, which are metabolically equipped to survive in especially hostile environments, still typically remain behind on the surface. These persister cells "re-seed" the surface, triggering biofilm re-growth.

Repeated cycles of biofilm removal and re-growth typically result in increasingly aggressive re-colonization by increasingly robust microbes.

As a result, biofilm control is especially difficult. However, the secretory compositions/cocktails described herein may be strong enough not only to kill the wide variety of robust microbes present, but also to effectively reach the surface underneath the biofilm such that the biofilm material is completely detached from the surface and can thus be removed (e.g., flushed) from the system. The cleaning compositions comprising secretory cocktails described herein are capable of penetrating and disrupting the biofilm matrix.

Typical surfaces can include those selected from the group consisting of metal, stainless steel, plastic, ceramic, porcelain, rubber, wood, concrete, cement, rock, marble, gypsum, and glass. The secretory composition/cocktails can contact the affected surface by any suitable means, such as lavage (e.g., washing with repeated injections of solution), misting, spraying, diluting, mopping, pouring, dipping, soaking, and combinations thereof. Contacting can be followed by removing detached debris from the system. Removing debris can be accomplished by any suitable means, including flushing, rinsing, draining, lavage, misting, spraying, mopping, wiping, rinsing, dipping, and combinations thereof, for example with a clean liquid such as water.

Acute infectious gastroenteritis is an extremely common illness, second in frequency only to acute respiratory illness among families (*New Engl J Med* (2007) 357; 11). Although it had long been suspected that such illnesses were caused by viruses, it was only after clinical and laboratory studies were carried out over the past three decades that causative viruses were identified. Among the most prominent are a novel group of viruses originally referred to as Norwalk-like agents—named after Norwalk, Ohio, where an outbreak of illness was caused by the prototype agent—and now called noroviruses. The biologic, physicochemical, and epidemiologic features of noroviruses present a serious challenge for infection control. Noroviruses are extremely infectious, and as few as 10 to 100 particles may be needed to cause infection. These viruses also are highly resistant to inactivation by freezing, heating to 60° C., exposure to chlorine in concentrations of 0.5 to 1.0 mg per liter, pH levels of 2.7, and treatment with ether, ethanol, or detergent-based cleaners. Thus, steaming or depuration of shellfish does not entirely eliminate the risk of transmission. Effective surface decontamination can be accomplished with solutions containing hypochlorite at 5000 ppm.

The primary control measures for norovirus outbreaks are environmental decontamination, prevention of contamination of water and food supplies (including restriction of the activity of sick food handlers), and possibly cohorting of infected patients in health care facilities or on cruise ships.

Surfaces that can be affected by biofilms or otherwise contaminated by disease causing agents can include those found in a variety of systems, such as those of the industrial, rail, marine, aerial, and household environments. Industrial systems can include those such as cooling water systems, heat exchangers, pulp and paper manufacturing, food processing systems, metalworking, photo processing, reverse osmosis membranes, water processing, flow channels, turbines, solar panels, pressurized water reactors, injection and spray nozzles, steam generators, process equipment, secondary oil recovery injection wells, and piping (e.g., drinking water).

Marine systems can include pipelines (e.g., of the offshore oil and gas industry), off-shore oil-rigs, and boat hulls. Marine-related environments include ship hallways and other public areas, air filters, air conditioning units, bathrooms, bedrooms and galleys. Aerial-related environments include air filters, air conditioning units, seats, and bathrooms of airplanes and airports.

Household systems include those surfaces found in swimming pools, toilets, household drains, and other household surfaces such as cutting surfaces, sinks, counter-tops, shower and bath surfaces, vases, pet food or water bowls, decorative water landscaping (e.g., fountains, ponds), and bird baths.

The concentration and amount of cleaning composition that is required to effectively treat and/or prevent biofilm or contamination in any particular situation will depend upon factors such as the specific alkali surfactant used, the level of biofilm or contamination, the level of treatment desired, the type of surface to be treated (e.g., household, various industrial settings), and length of time the cleaning composition will be in contact with the affected surface, all of which can be determined by one skilled in the art in view of this disclosure. Thus, it can be said that the amount of secretory composition/cocktail needed for any given surface will be an "effective amount". As used herein, an "effective amount" is the amount (i.e., concentration, quantity) of secretory composition/cocktail needed to achieve the desired level of treatment for a particular set of conditions. An effective amount may comprise decontaminating the affected surfaces up to 60%, 65%, 70%, 75%, 80%, 85%, 90%, 95%, or 100% of bacteria, fungal, biofilm, or viral growth. The composition/cocktail may be applied at different temperatures for different levels of activity, e.g. 15° C., 20° C., 30° C., 40° C., 50° C. or 60° C.

The cleaning composition can be in any suitable form. For example, product forms can include those such as detergents, powders (e.g., lyophilized powders), liquids, gels, pastes, and suspensions, as well as concentrates. Products or concentrates of such can be contained and deployed (e.g., dispensed and deposited upon a surface) with a variety of containers, vessels, tanks, or packages ranging from small (e.g. for household use) to large dose volumes (e.g., for industrial cleaning), wherein said containers can be reusable (e.g., plant tanks) to disposable (e.g., a small bottle or pouch). The container can contain enough product for a single use event or for multiple uses. The cleaning composition can be a fully-formulated ready-for-use product, or can require preparation before use. For example, the composition can be in the form of a kit comprising composition ingredients and instructions for preparation, or can be a concentrate for dilution either within or outside the container.

The cleaning compositions can optionally include any suitable adjunct ingredients, such as those known in the art for use in such cleaning compositions or washing detergents. For example, adjuncts can include, but are not limited to colorants and fragrances.

B. Agricultural, Medical, Manufacturing, and Environmental Products

Bacterial, yeast, viral, or fungal contamination of clinical, agricultural, manufacturing, or environmental products may lead to severe illness, and even death, if contacted by a subject or administered to a subject. Thus, in one aspect of the invention, the secretory compositions/cocktails of the present invention could be used to sterilize or decontaminate medical devices (such as catheters, surgical tools, stents, IVs), agricultural specimens (such as food, water supply, waste water, sludge, egg shells, plants, seeds, food containers), environmental specimens (such as lakes, and pools), and manufacturing samples (such as the machinery for processing samples). Non-limiting examples of manufacturing samples may also include sterile products and their components and intermediates that are manufactured for medical uses. In some embodiments, the secretory compositions/cocktails of the present invention could be used to sterilize wound dressings in remote or field locations. Other embodiments address increasing safety concerns to decontaminate both food products and the water supply from fungal, bacterial or viral contamination. Thus, the secretory compositions/cocktails may also apply to recreational facilities such as swimming pools and lakes, which may be contaminated with high levels of potentially pathogenic organisms or organisms that produce undesirable odors.

Another aspect of the invention relates to a method of breaking down urea comprising the step of contacting an agricultural, medical, manufacturing, and environmental product with an effective amount of any of the aforementioned secretory compositions/cocktails of the present invention. Such methods are based in part on the properties of the extremophilic fungi of the present invention to secrete ureases, which would help break down urea in farms and public places that have a lot of urine and/or feces. In some embodiments, the secretory compositions/cocktails of the present invention could be engineered to use ammonia and prevent the bad smells from urine and/or feces. In some embodiments, the secretory compositions/cocktails of the present invention could be used for fertilizer wastewaters. In some embodiments, the secretory compositions/cocktails of the present invention could be used for pH control and as a source of ammonia and carbon dioxide.

C. Biomass and Biofuels

Another aspect of the invention relates to a method of producing biofuels comprising the step of contacting a biomass with an effective amount of any of the aforementioned secretory compositions/cocktails of the present invention. In some embodiments, the biofuel may comprise alcohol, ethanol, biodiesel, bioethanol, bioalcohol, green diesel, biofuel gasoline, vegetable oil, biogas, syngas, solid biofuels, and the like. In a non-limiting example, the biomass can include, but is not limited to, lignocellulosic material woody biomass, such as recycled wood pulp fiber, sawdust, hardwood, softwood, algae, corn, sugarcane, sweet sorghum, trees, and combinations thereof; grasses, such as switch grass, cord grass, rye grass, reed canary grass, miscanthus, or a combination thereof; sugar-processing residues, such as but not limited to sugar cane bagasse; agricultural wastes, such as but not limited to rice straw, rice hulls, barley straw, corn cobs, cereal straw, wheat straw, canola straw, oat straw, oat hulls, and corn fiber; stover, such as but not limited to soybean stover, corn stover; and forestry wastes, such as but not limited to recycled wood pulp fiber, sawdust, hardwood (e.g., poplar, oak, maple, birch, willow), softwood, or any combination thereof. Other biomass includes agricultural wastes, such as manure, wastewater, cereal straws, including wheat straw, barley straw, canola straw and oat straw; corn fiber; stovers, such as corn stover and soybean stover; grasses, such as switch grass, reed canary grass, cord grass, and miscanthus; or combinations thereof.

In some embodiments, paper sludge is also a viable biomass for biofuel production. Paper sludge is solid residue arising from pulping and paper-making, and is typically removed from process wastewater in a primary clarifier. The cost of disposing of wet sludge is a significant incentive to convert the material for other uses, such as conversion to ethanol. Methods provided by the present invention are widely applicable. Moreover, the saccharification and/or fermentation products may be used to produce ethanol or higher value added chemicals, such as organic acids, aromatics, esters, acetone and polymer intermediates.

In other embodiment, the present invention relates to methods for biomass into ethanol, wherein said biomass is selected from the group consisting of grass, switch grass, cord grass, rye grass, reed canary grass, mixed prairie grass, miscanthus, sugar-processing residues, sugarcane bagasse, sugarcane straw, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, and combinations thereof.

D. Pharmaceutical/Medical Uses

Another aspect of the invention, relates to a method for treating a wound comprising the step of contacting the surface of the injured area with an effective amount of any of the aforementioned secretory compositions/cocktails. In some embodiments, the injured area is a cut, abrasion, open wound, sore, or abscess.

Another aspect of the invention, relates to a method for treating a skin or nail disorder comprising the step of contacting the affected surface of the skin or nail with an effective amount of any of the aforementioned secretory compositions/cocktails. In some embodiments, the skin or nail disorder is selected from the group consisting of acne, actinic keratosis, alopecia areata, athlete's foot, onchomychosis, atopic dermatitis, osmidrosis, eczema, fungal infection of the nails, psoriasis, rosacea, slow wound healing, folliculitis, keratosis pilaris, perioral dermatitis, angiofibromas, cutaneous inflammation, aging damage, dyschromia, premature greying hair, and seborrhea.

The secretory compositions/cocktails of the present invention may be specially formulated for administration in solid or liquid form, including those adapted for topical application, for example, as a cream, lotion, ointment, foam, or a controlled-release patch or spray applied to the surface of an affected or injured area. The desired concentration of the active compound in the secretory compositions/cocktails will depend on absorption, inactivation, and excretion and delivery rates of any enzymes, drugs, or compound in the secretory compositions/cocktail. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art. For example, a range of amounts of secretory compositions/cocktails are contemplated, including about 0.001, 0.01, 0.1, 0.5, 1, 10, 15, 20, 25, 50, 75, 100, 150, 200 or 250 mg or more of such compositions per kg body weight of the patient. Other amounts will be known to those of skill in the art and readily determined. In certain embodiments, the dosage of the secretory compositions/cocktails described above, will generally be in the range of about 0.001 mg to about 250 mg per kg body weight, specifically in the range of about 50 mg to about 200 mg per kg, and more specifically in the range of about 100 mg to about 200 mg per kg. In one embodiment, the dosage is in the range of about 150 mg to about 250 mg per kg. In another embodiment, the dosage is about 200 mg per kg.

In some embodiments, the molar concentration of the secretory compositions/cocktails described above, in a pharmaceutical composition will be less than or equal to about 2.5 M, 2.4 M, 2.3 M, 2.2 M, 2.1 M, 2M, 1.9M, 1.8M, 1.7M, 1.6 M, 1.5 M, 1.4M, 1.3 M, 1.2 M, 1.1 M, 1 M, 0.9 M, 0.8 M, 0.7M, 0.6 M, 0.5 M, 0.4 M, 0.3 M or 0.2 M. In some embodiments, the concentration of the secretory compositions/cocktails described above, will be less than or equal to about 0.10 mg/ml, 0.09 mg/ml, 0.08 mg/ml, 0.07 mg/ml, 0.06 mg/ml, 0.05 mg/ml, 0.04 mg/ml, 0.03 mg/ml or 0.02 mg/ml.

Actual dosage levels of the active ingredients in the compositions of the present invention may be varied so as to obtain an amount of the active ingredient, which is effective to achieve the desired therapeutic response for a particular patient, composition, and mode of administration, without being toxic to the patient.

The selected dosage level will depend upon a variety of factors including the activity of the particular therapeutic secretory compositions/cocktails in the formulation employed, or the ester, salt or amide thereof, the route of administration, the time of administration, the rate of excretion or metabolism of the particular therapeutic secretory compositions/cocktails being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. All aspects of the treatment, including supplements, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments, for example, to the amount(s) of agent administered and to the time of administration may be made based on these reevaluations.

Treatment may be initiated with smaller dosages which are less than the optimum dose of the compound. Thereafter, the dosage may be increased by small increments until the optimum therapeutic effect is attained.

Another aspect of the invention, relates to a method for providing a slow release of enzymes comprising the step of contacting the surface of an optical product with an effective amount of any of the aforementioned secretory compositions/cocktails. In some embodiments, the optical product is a contact lens.

Another aspect of the invention, relates to a method for removing urea comprising the step of contacting a medical device or clinical product with an effective amount of any of the aforementioned secretory compositions/cocktails. In some embodiments, the clinical product may comprise an artificial kidney dialyzates.

EXEMPLIFICATION

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Figure 1B:
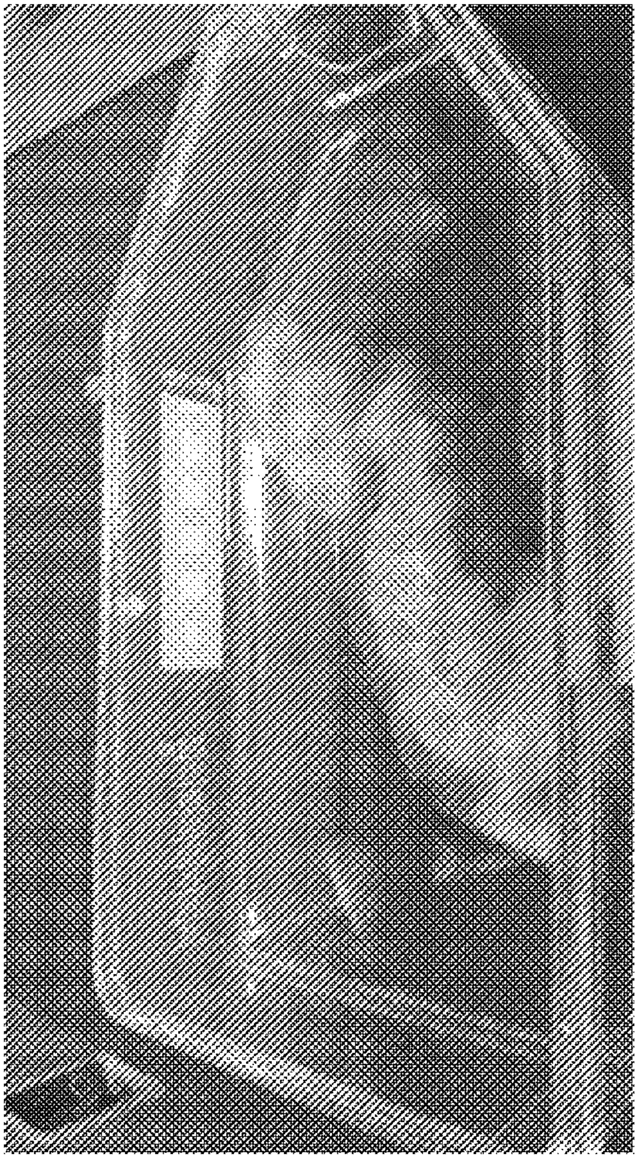
FIG. 1B shows mats of hyphae in a stationary culture.
Figure 2:
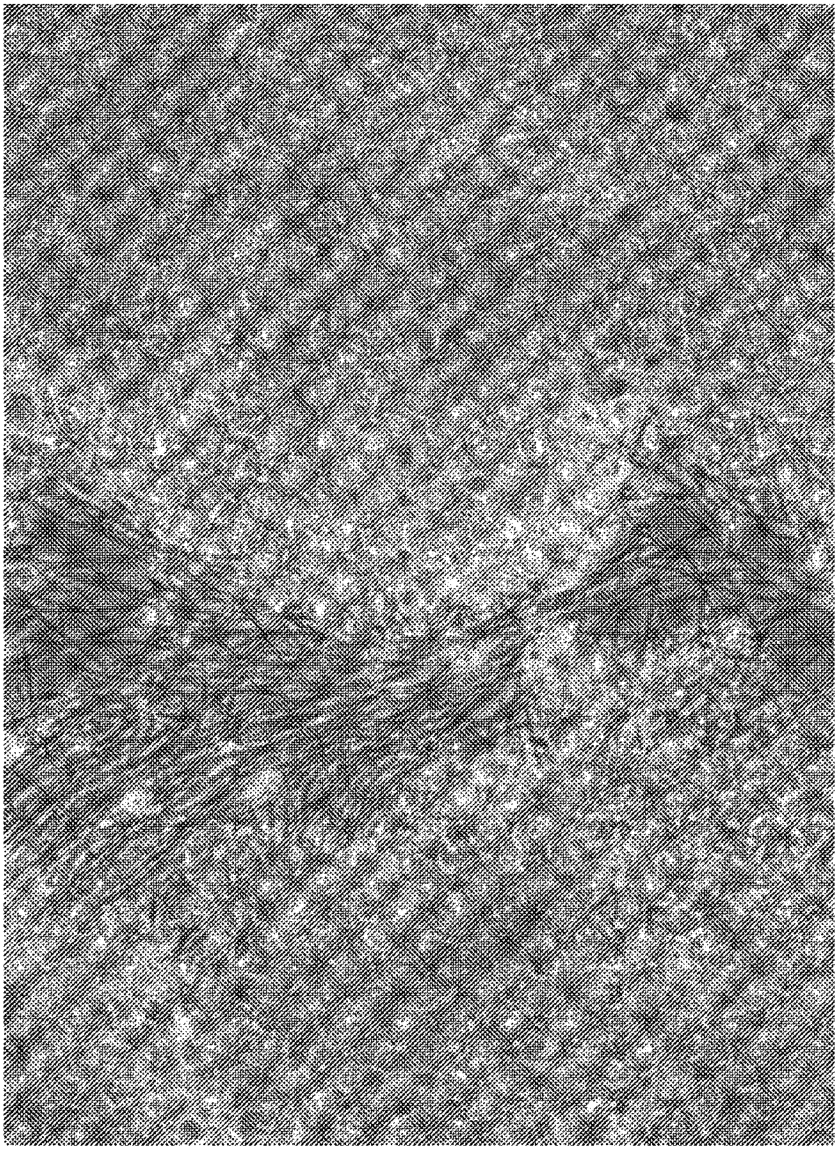
FIG. 2 depicts an image of the novel, extremophilic fungal species.

A novel, extremophilic fungal species was cultured, isolated, characterized and sequenced herein (FIG. 2). The whole genome of the novel, extremophilic fungal species has been sequenced and assembled. This novel fungal species secretes a cocktail of thermo-tolerant exo-enzymes. In addition, this fungal species digests cellular and genetic material in its surroundings under extreme temperatures. The organism has a variety of growth characteristics that can be exploited to provide a unique combination of heat-resistant lipases, proteases, RNases, and DNases and antimicrobials that destroy biological material within minutes upon contact (FIG. 1).

Non-naturally occurring countermeasures, such as addition of synthetic sources, have been used on the novel fungal species to generate novel cocktail of recombinant proteases and recombinant DNases.

Example 2

Figure 3:
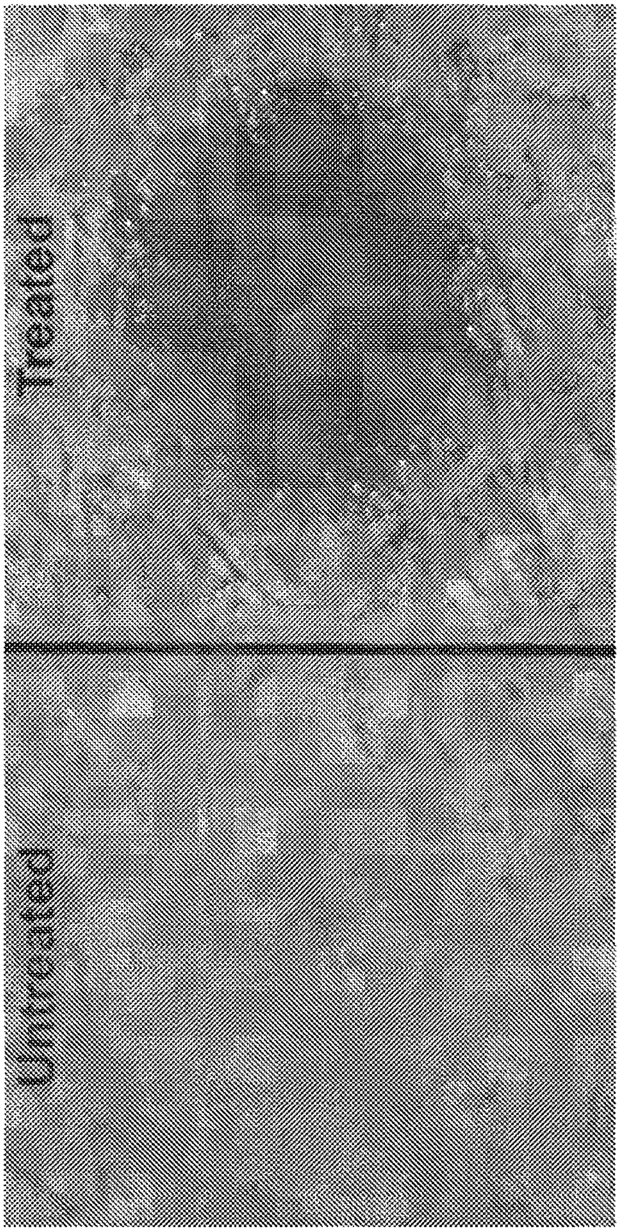
FIG. 3 shows an image of the bactericidal properties of the novel, extremophilic fungal species. The image shows a petri dish covered in bacteria and spotted with an enzyme composition isolated from the novel, extremophilic fungal species, and then grown for 15 hours. The treated dish (right panel) showed dramatic bactericidal properties when compared to the untreated dish (left panel).

Recent results show that the purified, concentrated, and stabilized secretory enzyme compositions/cocktails efficiently destroy human cells and bacteria. The cocktails work on a variety of surfaces at different temperatures. The cocktail of enzymes and essential salts should destroy most cell types and viruses, leaving behind an edible, non-toxic mixture of amino-acids and nucleotides (FIG. 3).

Example 3

Bacteria/Fungal Strains and Culture Conditions

The bacterial culture used in this study was *Bacillus anthracis* Sterne (−px02). Stock cultures of the organism were stored at −80° C. in brain heart infusion broth (BHI, RPI Cat #50-488-526) containing 25% (v/v) glycerol. Monthly, frozen stock cultures were transferred to working cultures by plating on BHI agar slants/plates and incubating at 37° C. for 24 hrs. Prior to each experiment, cultures were incubated overnight in BHI broth at 37° C. on a rotary shaker set at 150 RPM. All cultures were diluted with BHI broth to desired cell numbers.

The fungal culture used in this study was TM-417. Stock cultures of the organism were stored at −80° C. in yeast protein glucose broth (YpG; 0.4% yeast extract, 0.1% $K_2HPO_4$, 0.05% $MgSO_4$, 1.5% glucose, pH 7.3) containing 25% (v/v) glycerol. Monthly, frozen stock cultures were transferred to working cultures by plating on YPG agar plates and incubating at 55° C. for 4 days.

Preparation of Fungal Extract

Isolated cultures were transferred to Fernbach flasks containing 250 mL of DYpG (0.4% yeast extract, 0.1% $K_2HPO_4$, 0.05% $MgSO_4$, 1.5% glucose, 0.2% DNA, pH 7.3) broth. Each flask was placed on a shaker (115 RPMs) and incubated at 55° C. for three days. After three days, the flask was allowed to incubate statically for 2 additional days. Cell mass was removed from the sample by vacuum filtration through coarse filter paper (Fisherbrand Filter Paper P8). The filtrate was then filtered through sterile cheese cloth (06-665-28), then under vacuum through fine filter paper (Fisherbrand Filter Paper P4), frozen (−80° C.), and lyophilized. The lyophilized powder was stored at −20° C. and was the fungal extract (FE) used for all experiments.

Antimicrobial Activity of the Fungal Extract Against *B. anthracis* Sterne

Figure 4:
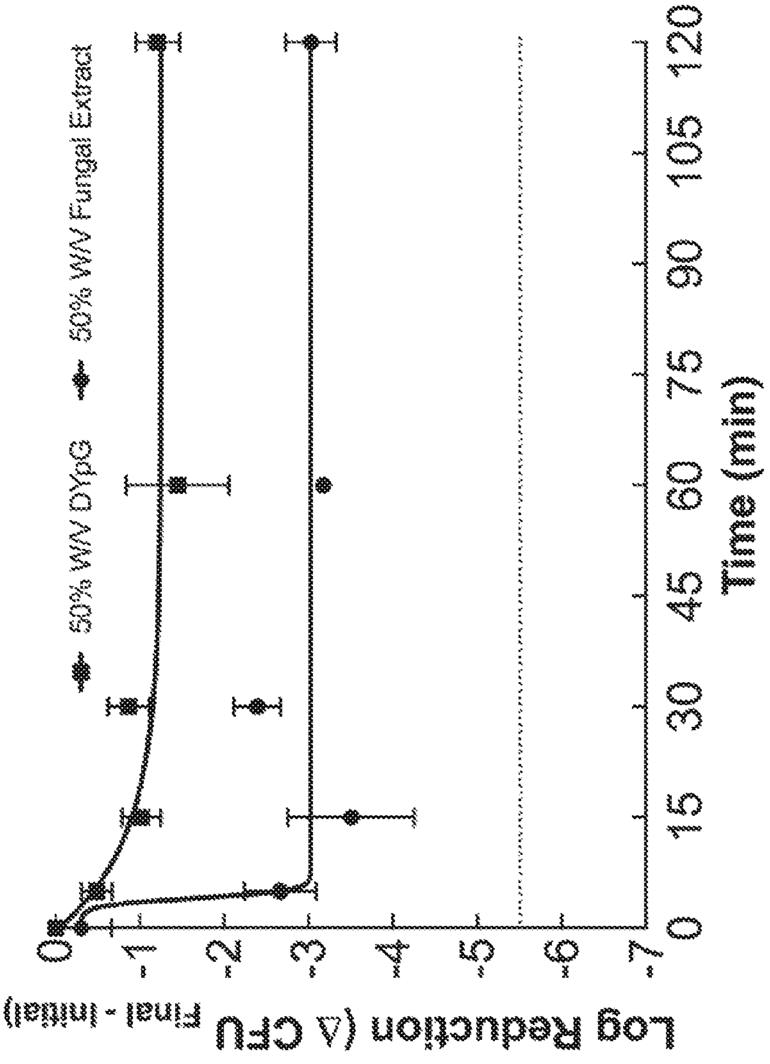
FIG. 4 shows antimicrobial activity of fungal extract against *B. anthracis* Sterne in saline.

The antimicrobial activity of the FE against *B. anthracis* Sterne in saline can be seen in FIG. 4. The FE was able to reduce the final cell numbers of *B. anthracis* Sterne levels by 3 logs following a 15-min treatment at room temperature. To see if non-inoculated growth media had an impact on *B. anthracis* Sterne, DypG growth media was lyophilized and applied to *B. anthracis* Sterne for the same amount of time and at the same concentration. Treatment of *B. anthracis* Sterne for 120 min with DypG growth media resulted in a 1 log reduction, demonstrating that the observed antimicrobial activity was related to the FE.

Lyophilized FE was added (% W/V) to saline inoculated with *B. anthracis* with a final cell density of 6 log CFU/mL and allowed to incubate at room temperature. Following incubation, the cells were washed twice with saline via centrifugation (13,400 RPM). The final washed pellet was suspended in brain-heart infusion (BHI) broth, serially diluted, and plated on BHI agar plates. A 3-tube most-probable-number enumeration in BHI broth was performed for samples that resulted in negative plate counts. All data points were performed in triplicate.

FIG. 4 shows the effect of the fungal extract (FE) (50% W/V) against *B. anthracis*. Briefly, lyophilized FE was added (50% W/V) to saline inoculated with *B. anthracis* for a final cell density of 6 log CFU/mL and allowed to incubate at room temperature. The treatment of *B. anthracis* with the FE resulted in a 3-log reduction after a 15 min treatment time. All data points were performed in triplicate. The limit of detection was 0.47 log CFU/mL, which correlated to a log reduction of −5.5 log CFU/mL as indicated by the dashed line. The limit of detection was 0.47 log CFU/mL, which correlated to a log reduction of −5.5 log CFU/mL as indicated by the dashed line.

Figure 5:
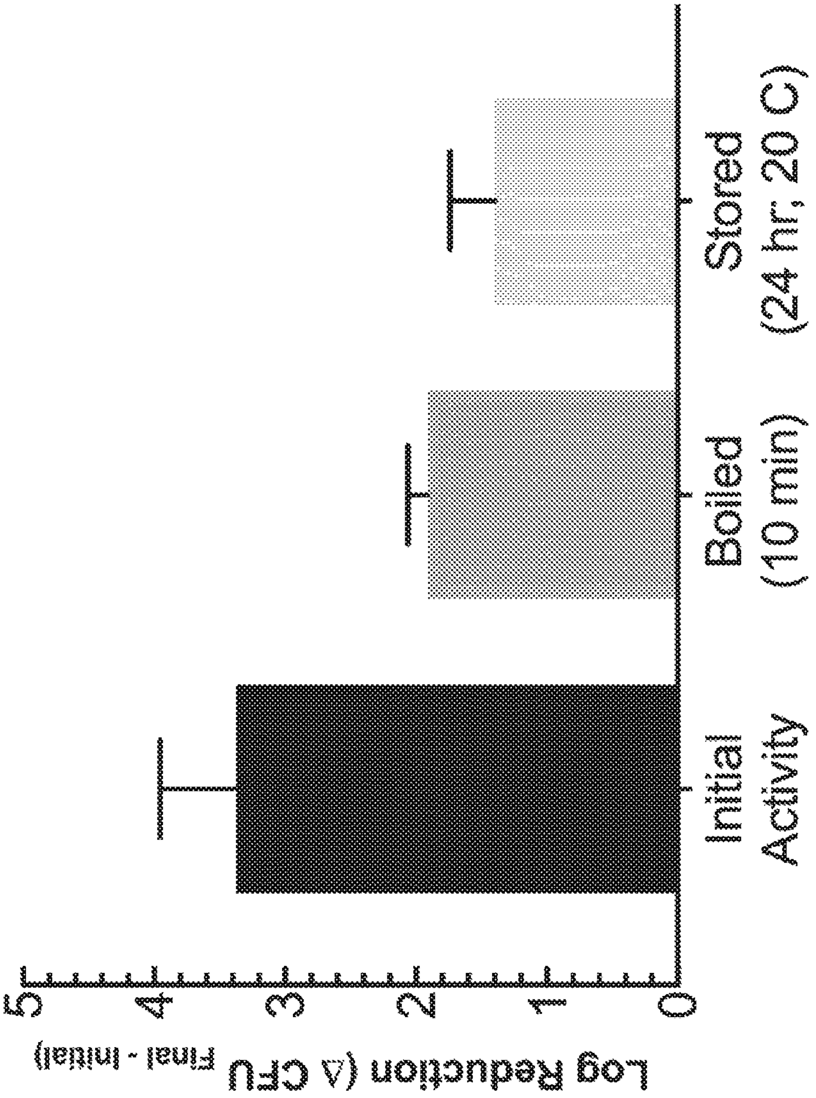
FIG. 5 shows the effect of boiling and room temperature storage on the efficacy of fungal extract against *B. anthracis*.

Effect of Temperature and Storage on the Efficacy of the Fungal Extract Against *B. anthracis* Sterne To determine the stability, the FE was either boiled for 10 min or stored at 20° C. for 24 hrs. The prolonged storage and boiling of the FE resulted in a dramatic decrease in antimicrobial activity (FIG. 5). Sample that were boiled had a 44% decrease in efficacy against *B. anthracis* Sterne when compared to the control. The efficacy of FE that was stored for 24 hr at 20° C. was reduced by over 59%. Since the antimicrobial activity of the FE is believed to be mostly protein based, boiling the FE for 10 min may have denatured some of the active proteins. It is known that TM-417 produces a large amount of proteases. Prolonged unrefrigerated storage of the FE may have allowed the native proteases to act on the functional proteins present in the extract, decreasing the overall effectiveness of the FE over time.

Prior to testing, two batches of FE (50% W/V) were made: 1) FE that was boiled for 10 mins, and 2) FE that sat at room temperature for 24 hr. *B. anthracis* was added to 5 mL of each FE batch for a final cell number of 6 log CFU/mL and allowed to incubate for 30 min at room temperature. Initial activity was determined by incubating *B. anthracis* (6 log CFU/mL) for 30 mins in a freshly prepared solution of 50% W/V FE. Following incubation, cells were washed twice with saline via centrifugation (13,400 RPM). The final washed pellet was suspended in brain-heart infusion (BHI) broth, serially diluted, and plated on BHI agar plates.

FIG. 5 shows the effect of boiling and room temperature storage on the efficacy of the FE against *B. anthracis*. Boiling and storage at room temperature greatly reduced the efficacy of the FE against *B. anthracis*. All data points were performed in triplicate.

Figure 6:
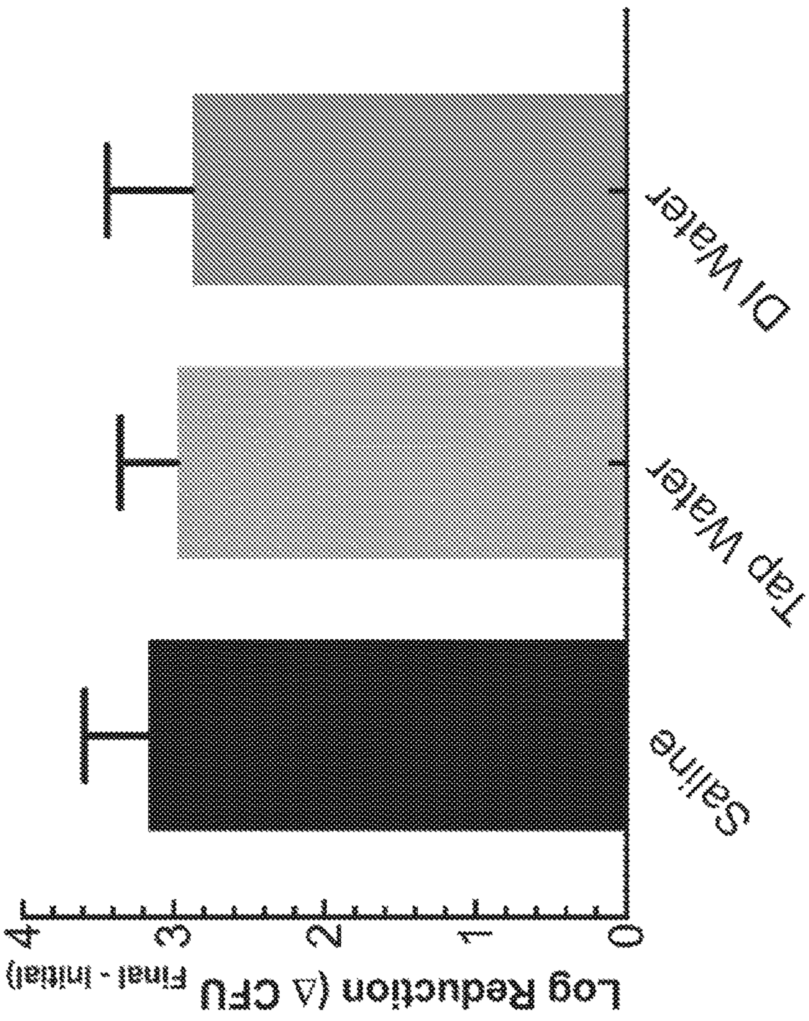
FIG. 6 shows the influence of water type on the efficacy of fungal extract against *B. anthracis*.

Effect of Water on the Efficacy of the Fungal Extract Against *B. anthracis* Sterne The activity of an enzymes is usually impacted by the environment in which they are reconstituted. Since this extract is from a thermophilic organism, it was theorized that function proteins produced by TM-417 would be able to tolerate non-buffered environments. To test this theory, the FE (50% W/V) was dissolved in either saline, tap water, or distilled water and tested against *B. anthracis* Sterne (FIG. 6). Dissolving the FE in saline, tap water, or distilled water had no impact on its effectiveness against *B. anthracis* Sterne.

Lyophilized FE was added to either saline, tap water, or reverse osmosis water for a final concentration of 50% W/V. The solution was inoculated with *B. anthracis* for a final cell density of 6 log CFU/mL and allowed to incubate at room temperature for 1 hr. Following incubation, the cells were washed twice with saline via centrifugation (13,400 RPM). The final washed pellet was suspended in brain-heart infusion (BHI) broth, serially diluted, and plated on BHI agar plates.

FIG. 6 shows the influence of water type on the efficacy of FE against *B. anthracis*. The FE (50% W/V) was dissolved in either saline, tap water, or distilled water and its ability to inactivate *B. anthracis* was assessed. It was found that there was not significant difference between the antimicrobial activity of the FE when dissolved in three types of water. All data points were performed in triplicate.

Antimicrobial Efficacy of FE Combined with Lysozyme and Proteinase K Against *B. anthracis* Sterne To see if the effectiveness of the FE against *B. anthracis* Sterne could be improved, the FE was supplemented with a combination of proteinase K and lysozyme (10 or 100 units/mL; FIG. 7) or ampD (6 μg/μL) and phi29 lysozyme (2 μg/μL) (FIG. 8). The supplementation of the FE with proteinase K and lysozyme greatly enhanced the FE's antimicrobial activity at 37° C. When supplemented with either 10 or 100 units/mL proteinase K and lysozyme, reductions >2.5 logs were observed when compared to viable cell counts from the untreated samples following a 4 hr treatment. Increasing lysozyme and proteinase K concentrations from 10 units/mL to 100 units/mL did not increase the antimicrobial activity. The supplementation of the FE with ampD (6 μg/μL) and phi29 lysozyme (2 μg/μL) resulted in >5 log reduction in viable cell counts when treated for 2 hr at either 20° C. or 37° C.

Lyophilized FE was added (10% W/V) to saline containing Lysozyme (10 or 100 units/mL) and Proteinase K (10 or 100 units/mL) and inoculated with *B. anthracis* with a final cell density of 6 log CFU/mL and allowed to incubate for 4 hr at either room temperature or 37° C. Following incubation, the cells were washed twice with saline via centrifugation (13,400 RPM). The final washed pellet was suspended in brain-heart infusion (BHI) broth, serially diluted, and plated on BHI agar plates. A 3-tube most-probable-number enumeration in BHI broth was performed for samples that resulted in negative plate counts.

Figure 7A:
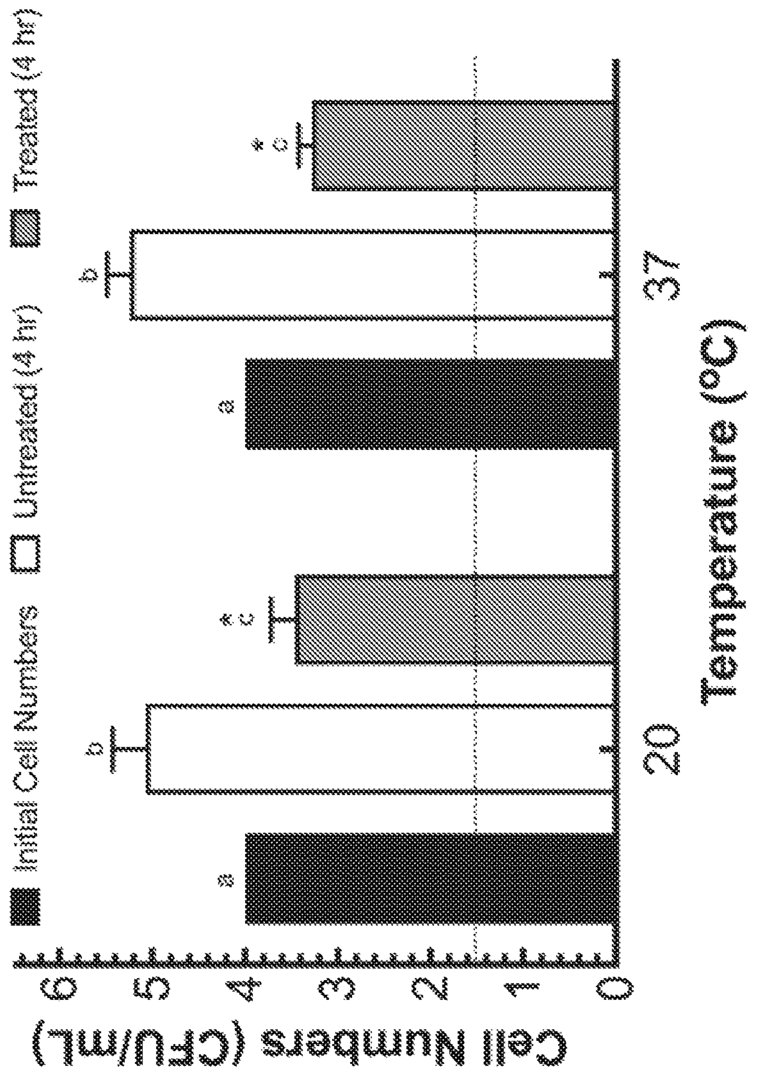
FIG. 7A shows the antimicrobial activity of fungal extract against *B. anthracis* Sterne.
Figure 7B:
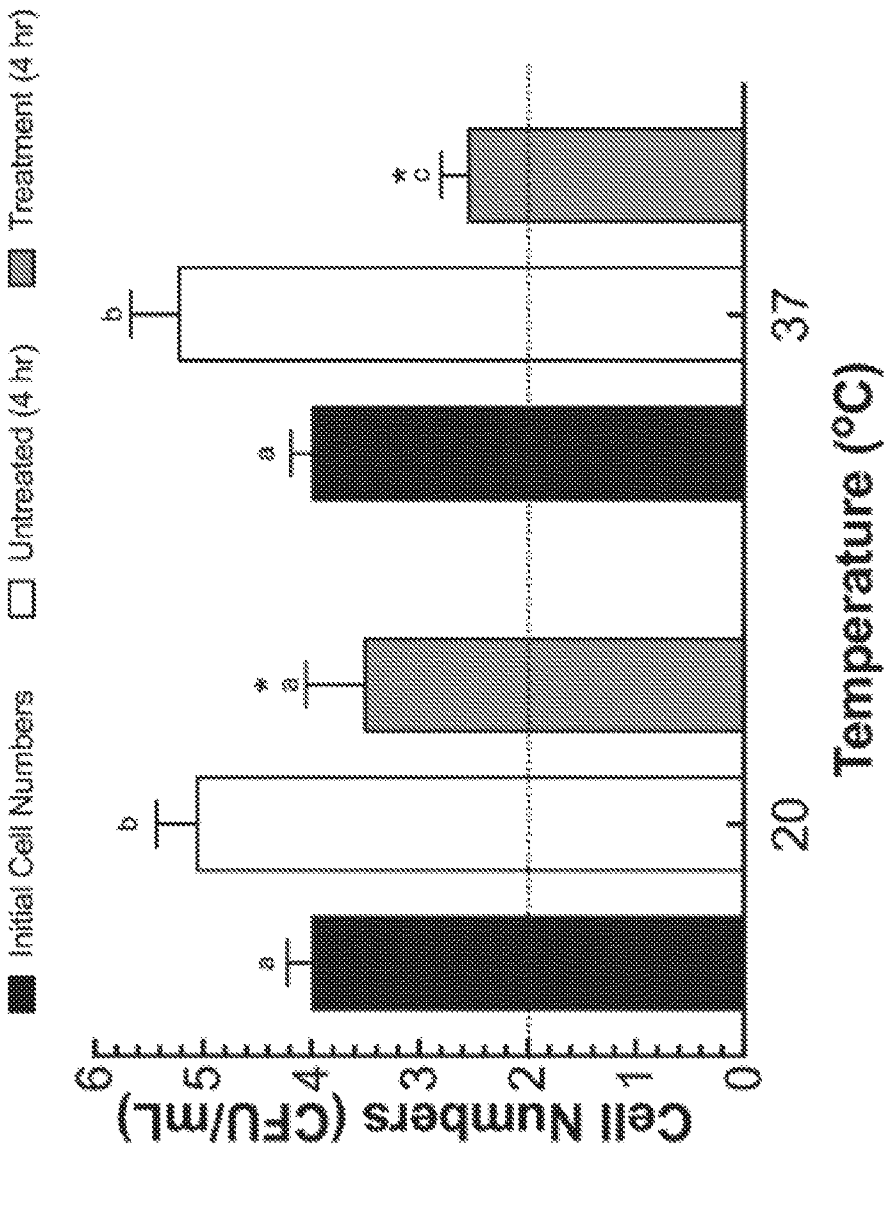
FIG. 7B shows the antimicrobial activity of fungal extract with 10 units/mL of proteinase K and lysozyme.
Figure 7C:
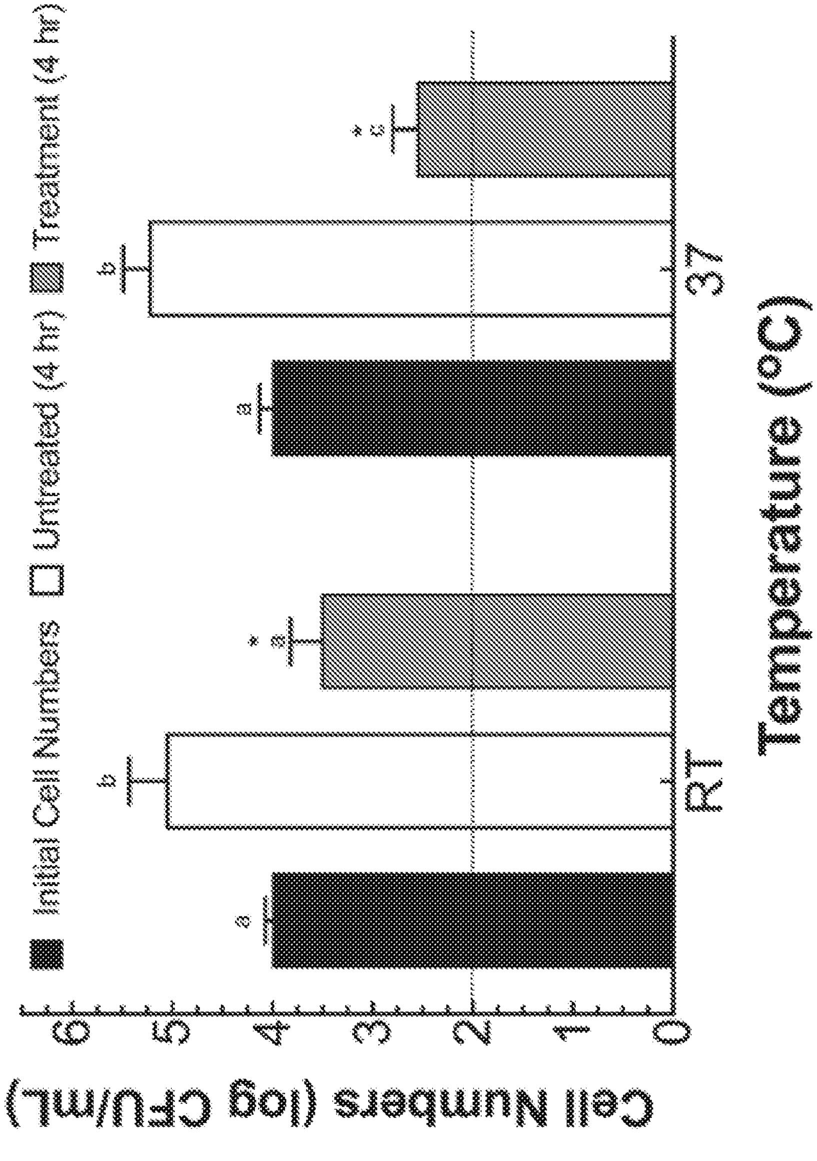
FIG. 7C shows the antimicrobial activity of fungal extract with 100 units/mL of proteinase K and lysozyme.
Figure 8:
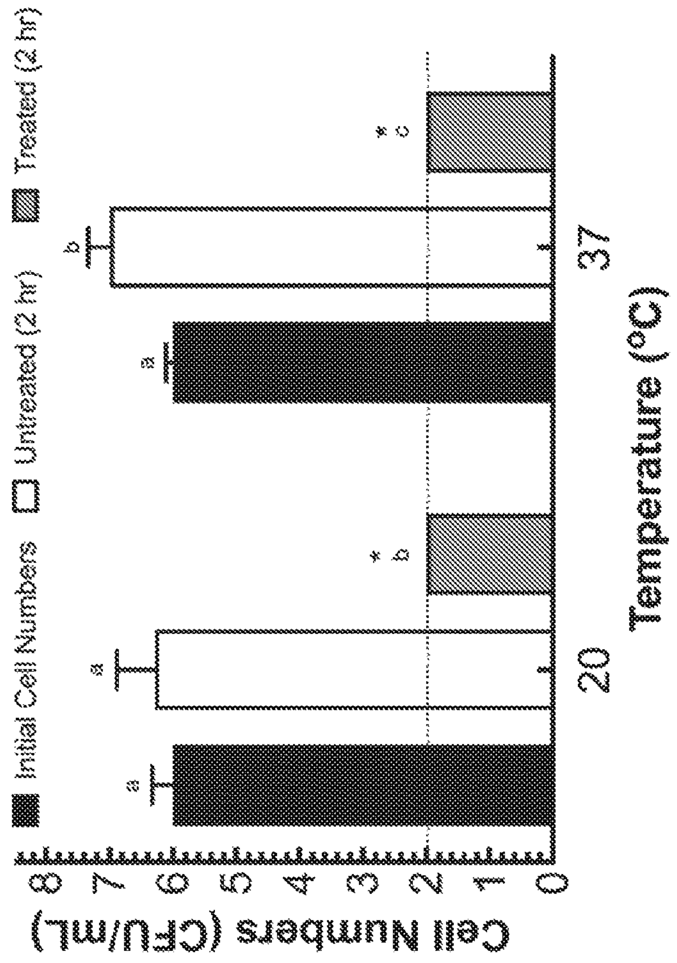
FIG. 8 shows antimicrobial activity of fungal extract supplemented with ampD and phi29 lysozyme against *B. anthracis* Sterne.

FIG. 7A-C shows the antimicrobial activity of the FE (FIG. 7A) and the FE supplemented with either 10 units/mL (FIG. 7B) or 100 units/mL (FIG. 7C) of proteinase K and lysozyme against *B. anthracis* Sterne. Antimicrobial activity was assessed at 20° C. and 37° C. Supplementation with proteinase K and lysozyme enhanced the antimicrobial activity of the FE. All data points were performed in triplicate. Treatments were compared to initial cells numbers using a one-tail t-test with a 95% confidence interval. Treatments grouped using Tukey's-test with a 95% confidence interval. All data points were performed in triplicate. The limit of detection was 0.47 log CFU/mL, which correlated to a log reduction of −5.5 log CFU/mL as indicated by the dashed line.

Antimicrobial Efficacy of FE Combined with ampD and Phi29 Lysozyme Against *B. anthracis* Sterne Lyophilized FE was added (10% W/V) to saline containing ampD (6 μg/μL) and phi29 lysozyme (2 μg/μL) and inoculated with *B. anthracis* with a final cell density of 6 log CFU/mL and allowed to incubate for 2 hr at either room temperature or 37° C. Following incubation, the cells were washed twice with saline via centrifugation (13,400 RPM). The final washed pellet was suspended in brain-heart infusion (BHI) broth, serially diluted, and plated on BHI agar plates. A 9-tube most-probable-number enumeration in BHI broth was performed for samples that resulted in negative plate counts. FIG. 8 shows antimicrobial activity of the FE supplemented with 6 μg/μL of ampD and 2 μg/μL of phi29 lysozyme against *B. anthracis* Sterne. Antimicrobial activity was assessed at 20° C. and 37° C. All data points were performed in triplicate. Treatments were compared to initial cells numbers using a one-tail t-test with a 95% confidence interval. Treatments grouped using Tukey's-test with a 95% confidence interval. All data points were performed in triplicate. The limit of detection was 0.47 log CFU/mL, which correlated to a log reduction of −5.5 log CFU/mL as indicated by the dashed line.

Antimicrobial Efficacy of FE Combined with AmpD and Phi29 Lysozyme Against *B. anthracis* Sterne on Surfaces A potential application of the FE would be to use it to inactive *B. anthracis* Sterne on a variety of surfaces such as stainless steel (FIG. 9) and glass (FIG. 10). *B. anthracis* Sterne was dried onto the surface of glass or stainless steel coupons and treated with FE supplemented with ampD (6 μg/μL) and phi29 lysozyme (2 μg/μL). The supplemented FE reduced viable *B. anthracis* Sterne levels on glass and stainless steel by more than 3 logs at room temperature following a 120 min and 30 min treatment respectively.

Figure 9:
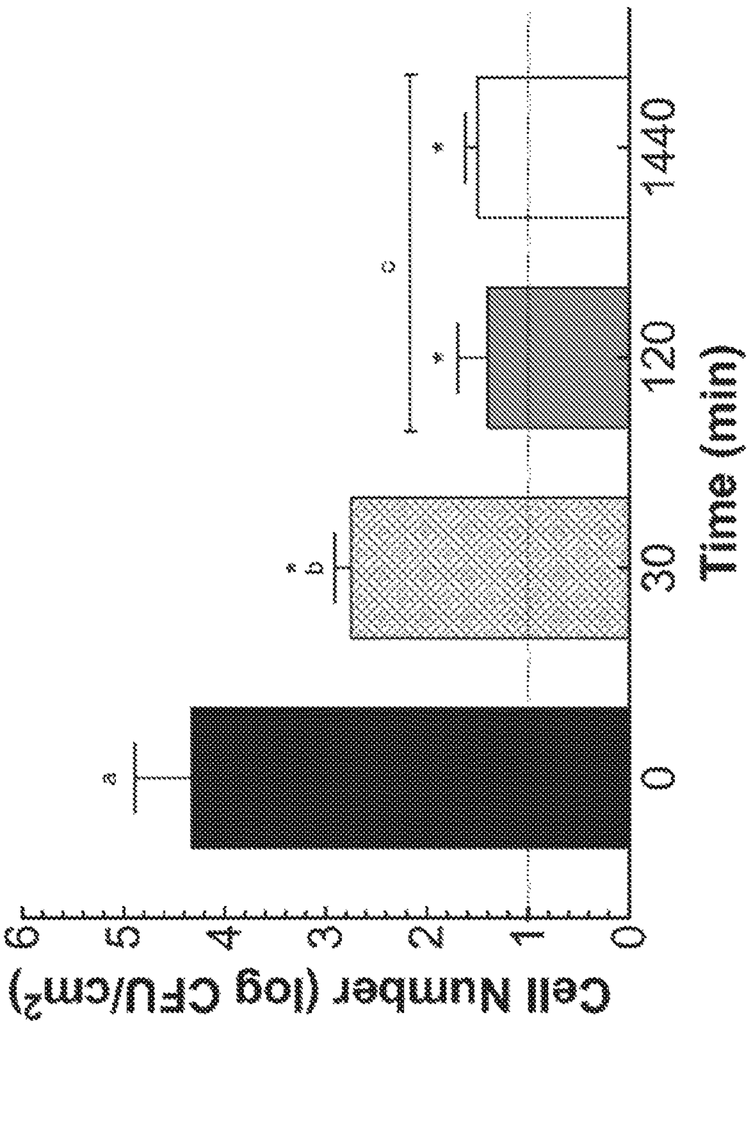
FIG. 9 shows the efficacy of fungal extract supplemented with ampD and phi29 lysozyme against *Bacillus anthracis* on stainless steel.
Figure 10:
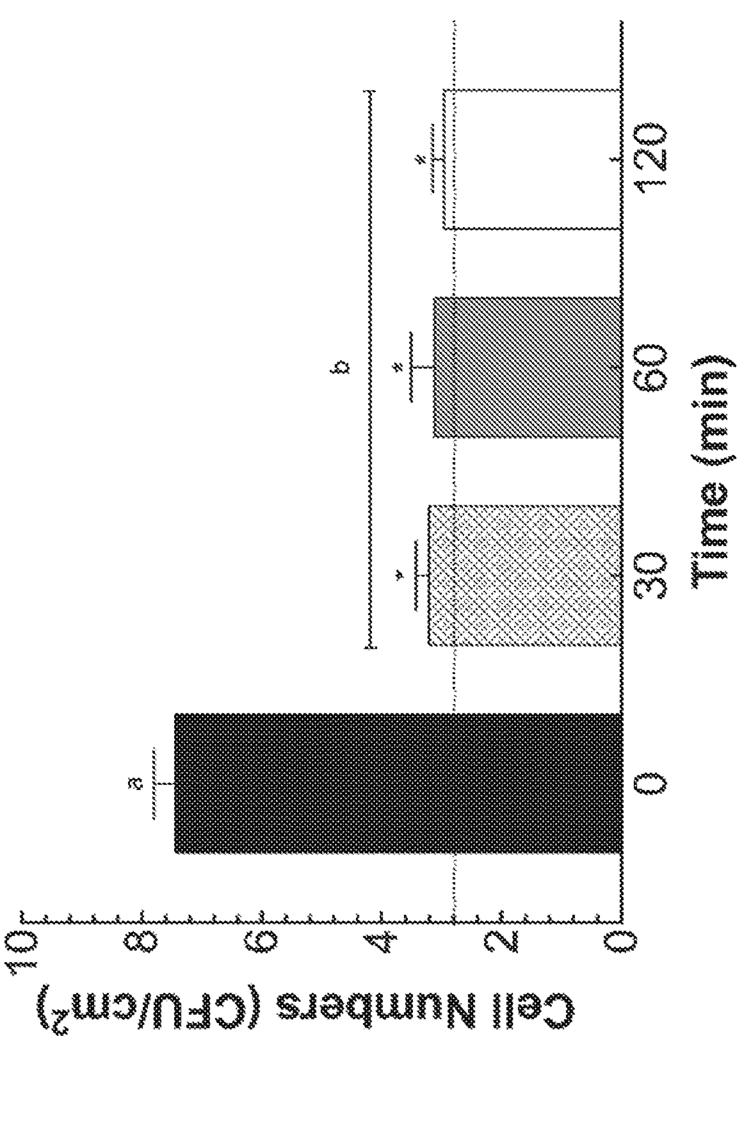
FIG. 10 shows the efficacy of fungal extract supplemented with ampD and phi29 lysozyme against *Bacillus anthracis* on glass.

Sterile stainless steel (304) or glass coupons were placed in a sterile glass petri dish containing sterile filter paper and inoculated for a final pathogen levels of 4 or 7 log CFU/$cm^2$ respectively. The coupons were dried overnight in a biosafety cabinet at room temperature. The initial numbers of *B. anthracis* Sterne on the coupons were determined by vortexing the coupons in sterile maximum recovery diluent (MRD) for 10 seconds at maximum speed. The inoculated chips were treated by applying 100 μL of FE (10% W/V) containing ampD (6 μg/μL) and phi29 lysozyme (2 μg/μL) to the coupons surface and allowing it to soak for a specific period of time. After treatment, the chips were immediately transferred into 30 mL of sterile MRD and soaked for 10 minutes followed by vortexing at maximum speed (10 sec). A dilution series was performed and plated BHI agar. A 3-tube most probable number assay (MPN) was used for samples that resulted in negative plate counts. Samples were incubated overnight at 37° C. Following incubation, the samples with positive MPN were streaked onto BHI agar for confirmation. FIG. 9 shows the efficacy of FE supplemented with 6 μg/μL of ampD and 2 μg/μL of phi29 lysozyme against *Bacillus anthracis* on stainless steel (304) coupons. Treatments were compared to initial cells numbers using a one-tail t-test with a 95% confidence interval. Treatments grouped using Tukey's-test with a 95% confidence interval. FIG. 10 shows the efficacy of FE supplemented with 6 μg/μL of ampD and 2 μg/μL of phi29 lysozyme against *Bacillus anthracis* on glass coupons. Treatments were compared to initial cells numbers using a one-tail t-test with a 95% confidence interval. Treatments grouped using Tukey's-test with a 95% confidence interval.

REFERENCES

1. Landry K S, Levin R E. Characterization of a recently purified thermophilic DNase from a novel thermophilic fungus. *Appl Biochem Biotechnol.* (2014) 173(7): 1587-96.
2. Landry K S, Vu A, Levin R E. Purification of an inducible DNase from a thermophilic fungus. *Int J Mal Sci.* (2014) 15(1):1300-14.
3. Landry K S, Levin R E. Purification and characterization of iso-ribonucleases from a novel thermophilic fungus. *Int J Mal Sci.* (2014) 15(1):944-57.
4. Landry K S, Levin R E. Development of a novel affinity membrane purification system for deoxyribonuclease. *Appl Biochem Biotechnol.* (2014) 172(4):1964-9.
5. Tullis, R H and Rubin, H. Calcium protects DNase I from Proteinase K: A new method for the removal of contaminating RNase from DNase. *Analytical Biochemistry.* (1998) 107:260-264

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method for reducing an amount or an activity of microorganisms in a wound on a subject, comprising:

contacting the wound comprising the microorganisms with a composition comprising one or more enzymes derived from TM-417, thereby reducing the amount or the activity of the microorganisms.

2. The method of claim 1, wherein the one or more enzymes comprise at least one enzyme selected from the group consisting of urease, DNase, RNase, exonuclease, endonuclease, ribonuclease, amylase, acetoin reductase, an indole-3-acetamide hydrolase, a tryptophan monooxygenase, an acetolactate synthetase, an α-acetolactate decarboxylase, a pyruvate decarboxylase, a diacetyl reductase, a butanediol dehydrogenase, an aminotransferase, a tryptophan decarboxylase, an amine oxidase, an indole-3-pyruvate decarboxylase, an indole-3-acetaldehyde dehydrogenase, a tryptophan side chain oxidase, a nitrile hydrolase, a nitrilase, a peptidase, a protease, an adenosine phosphate isopentenyltransferase, a phosphatase, an adenosine kinase, an adenine phosphoribosyltransferase, CYP735A, a 5'ribonucleotide phosphohydrolase, an adenosine nucleosidase, a zeatin cis-trans isomerase, a zeatin O-glucosyltransferase, a β-glucosidase, a cis-hydroxylase, a CK cis-hydroxylase, a CK N-glucosyltransferase, a 2,5-ribonucleotide phosphohydrolase, an adenosine nucleosidase, a purine nucleoside phosphorylase, a zeatin reductase, a hydroxylamine reductase, a 2-oxoglutarate dioxygenase, a gibberellic 2B/3B hydrolase, a gibberellin 3-oxidase, a gibberellin 20-oxidase, a chitosanase, a chitinase, a β-1,3-glucanase, a β-1,4-glucanase, a β-1,6-glucanase, an aminocyclopropane-1-carboxylic acid deaminase, chitosanase, a cellulase, a lipase, a lignin oxidase, a glycoside hydrolase, a phosphatase, a nitrogenase, a nuclease, an amidase, a nitrate reductase, a nitrite reductase, an amylase, an ammonia oxidase, a ligninase, a glucosidase, a phospholipase, a phytase, a pectinase, a glucanase, a sulfatase, a xylanase, an endocellulase, an exocellulase, a β-glucosidase, phospholipase, acetate kinase, phosphotransacetylase, lactate dehydrogenase, pyruvate decarboxylase (PDC), alcohol dehydrogenase (ADH), xylose isomerase, xylulokinase, L-arabinose isomerase, L-ribulose-5-phosphate 4-epimerase, a glycan strand-cleaving enzyme/glycosidase, N-acetylglucosaminidase, acetylmuramyl-L-alanine amidase, lysozyme, lytic transglycosylase and peptidoglycan endopeptidase.

3. The method of claim 1, wherein the one or more enzymes comprise two or more enzymes.

4. The method of claim 1, wherein the one or more enzymes have at least about a 25-fold increase in specific activity when purified using size exclusion chromatography in combination with an affinity based membrane purification system, at least about a 100-fold increase in specific activity when purified using size exclusion chromatography in combination with an affinity based membrane purification system.

5. The method of claim 1, wherein the one or more enzymes is at least about 50% pure.

6. The method of claim 1, wherein the composition comprises ampD.

7. The method of claim 1, wherein the composition comprises lysozyme.

8. The method of claim 1, wherein the composition comprises phi29 lysozyme.

9. The method of claim 1, wherein the activity of the microorganisms comprises pathogenicity, viability, reproduction, metabolism, or toxin production.

10. The method of claim 1, wherein the amount or the activity of the microorganisms is reduced by at least about 10%.

11. The method of claim 1, wherein the wound on the subject is a cut, abrasion, open wound, sore, or abscess.

12. The method of claim 11, wherein the subject suffers from slow wound healing.

13. The method of claim 1, wherein the subject is an animal.

14. The method of claim 1, wherein the subject is a mammal.

15. The method of claim 1, wherein the subject is a human.

16. The method of claim 1, wherein the one or more enzymes comprise a protease.

* * * * *